United States Patent
Li et al.

(10) Patent No.: US 9,695,174 B2
(45) Date of Patent: Jul. 4, 2017

(54) INHIBITOR OF BREAST CANCER RESISTANCE PROTEIN (BCRP)

(71) Applicant: Millennium Pharmaceuticals, Inc., Cambridge, MA (US)

(72) Inventors: Yuexian Li, Lexington, MA (US); Shimoga R. Prakash, Southborough, MA (US); Cindy Qi Xia, Acton, MA (US); Mingxiang M. Liao, Medford, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/025,906

(22) PCT Filed: Oct. 6, 2014

(86) PCT No.: PCT/US2014/059307
§ 371 (c)(1),
(2) Date: Mar. 30, 2016

(87) PCT Pub. No.: WO2015/054132
PCT Pub. Date: Apr. 16, 2015

(65) Prior Publication Data
US 2016/0214984 A1 Jul. 28, 2016

Related U.S. Application Data

(60) Provisional application No. 61/970,543, filed on Mar. 26, 2014, provisional application No. 61/887,476, filed on Oct. 7, 2013.

(51) Int. Cl.
*C07D 471/14* (2006.01)
*A61K 31/4985* (2006.01)
*G01N 33/50* (2006.01)

(52) U.S. Cl.
CPC ........ *C07D 471/14* (2013.01); *A61K 31/4985* (2013.01); *G01N 33/5011* (2013.01); *G01N 33/5088* (2013.01); *G01N 2333/70596* (2013.01)

(58) Field of Classification Search
CPC .................................................. C07D 471/14
See application file for complete search history.

(56) References Cited

U.S. PATENT DOCUMENTS

2008/0312250 A1  12/2008  Breedveld et al.
2012/0052005 A1   3/2012  Ding et al.

OTHER PUBLICATIONS

Allen, et al., "Potent and Specific Inhibition of the Breast Cancer Resistance Protein Multidrug Transporter in Vitro and in Mouse Intestine by a Novel Analogue of Fumitremorgin $C^1$," Mol Cancer Ther, 2002, 1:417-425.

Chen et al., "Total Synthesis of (±)—Alantrypinone by Hetero Diels—Alder Reaction," J Org Chem, 2004, 69:79-85.

Li et al., "Synthesis of Potent BCRP Inhibitor—Ko143," Tetrahedron Letters, 2008, 49:1480-1483.

Li et al., "Synthesis of a New Inhibitor of Breast Cancer Resistance Protein with Significantly Improved Pharmacokinetic Profiles," Bioorganic & Medicinal Chemistry Letters, 2016, 26:551-555.

Wakasugi, et al., "$Me_2NSO_2Cl$ and N,N-dimethylamines; a Novel and Efficient Agent for Esterification, Amidation Between Carboxylic Acids, and Equimolar Amounts of Alcohols and Amines," Tetrahedron Letters, 2001, 42:7427-7430.

Xia, et al., "Expression, Localization, and Functional Characteristics of Breast Cancer Resistance Protein in CACO-2 Cells," Drug Metabolism and Disposition, 2005, 33:637-643.

Xia et al., "Selectivity of Commonly Used CYP3A4 and Efflux Transporter Inhibitors," Poster, Millennium Pharmaceuticals, Inc., 2005, 1 page.

*Primary Examiner* — James D Anderson
(74) *Attorney, Agent, or Firm* — McNeill Baur PLLC

(57) ABSTRACT

Disclosed are compounds that inhibit breast cancer resistance protein (BCRP), of which compound (I-1), ((3S,6S,12aS)-6-isobutyl-9-methoxy-3-methyl-2,3,6,7,12,12a-hexahydropyrazino[1',2':1,6]pyrido[3,4-b]indole-1,4-dione) or a pharmaceutically acceptable salt thereof, and the compound 12, ((3S,6S,12aS)-6-isobutyl-9-methoxy-3,10-dimethyl-2,3,6,7,12,12a-hexahydropyrazino[1',2':1,6]pyrido[3,4-b]indole-1,4-dione) or a pharmaceutically acceptable salt thereof. Also disclosed are methods of inhibiting BCRP or decreasing BCRP activity and methods of determining potential BCRP substrates.

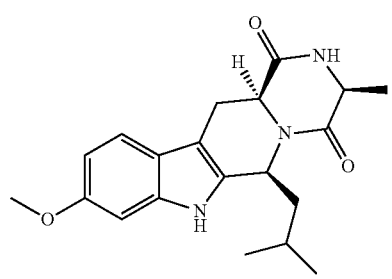

(I)

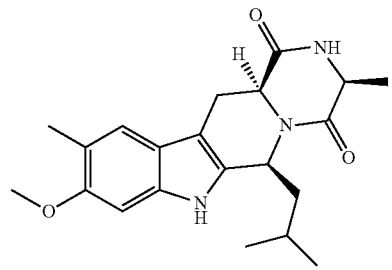

(12)

20 Claims, No Drawings

INHIBITOR OF BREAST CANCER RESISTANCE PROTEIN (BCRP)

RELATED APPLICATIONS

This application claims priority to U.S. Provisional Application No. 61/887,476 filed on Oct. 7, 2013 and to U.S. Provisional Application No. 61/970,543 filed on Mar. 26, 2014. The entire contents of the foregoing applications are incorporated herein by reference.

BACKGROUND

Resistance to anticancer agents is a major cause of chemotherapeutic failure in cancer. (M. K. Rosenberg et al., *Structure*, 2010, 18, 482.) The 75 kDa human breast cancer resistance protein (BCRP) is a polytopic plasma membrane transport protein that has been detected in many drug-resistant cell lines, solid tumors, and hematological malignancies. BCRP (encoded by ABCG2, also known as ABCG2 and MXR (mitoxantrone-resistance protein)), an ATP-binding cassette transporter, is one of the most important transporters involved in multi-drug resistance. (Id.) BCRP expression in cancer cells confers drug-resistance in leukemia and higher levels are reported in solid tumors from the adenocarcinomas of the digestive tract, endometrium, lung and melanoma. Frequent expression of the multi-drug resistance-associated protein BCRP/MXR/ABCP/ABCG2 in human tumours detected by the BXP-21 monoclonal antibody in paraffin-embedded material. (Diestra, J. E., et al., *J Pathol*, 2002. 198(2): p. 213-9.)

Ko143 is a novel fumitremorgin C analogue and reported to be a more potent and specific inhibitor than other known inhibitors of BCRP such as novobiocin, tariquidar (XR9576), elacridar (GF120918), gefitinib and imatinib. (J. D. Allen et al., *Mol. Cancer Ther.*, 2002, 1, 417; A. Pick et al., *Bioorg. Med. Chem. Lett.*, 1999, 9, 595.) Importantly, Ko143 is nontoxic at effective in vitro and in vivo concentrations. (J. D. Allen et al.) Subsequent routes for the synthesis of Ko143 have been reported. (Y. Li et al., *Tetrahedron Lett.*, 2008, 49, 1480; C. Q. Xia et al., Selectivity of commonly used CYP3A4 and efflux transporter inhibitors. The 13th North American ISSX Meeting, Maui, Hi. (2005). *Drug Metabolism Review*. Vol 37 (suppl 2): p304 (#556)).

According to draft guidance from the United States Food and Drug Administration ("FDA"), both P-gp (P-glycoprotein, ABCB1, MDR1), another ATP-binding cassette transporter, and BCRP are expressed in the gastrointestinal tract, liver, and kidney, and have a role in limiting oral bioavailability. Therefore, investigational drugs with low permeability should be evaluated in vitro to determine whether they are potential substrates of P-gp or BCRP. (Notice, *Draft Guidance for Industry on Drug Interaction Studies—Study Design, Data Analysis, Implications for Dosing, and Labeling Recommendations*, 77 FR 9946, Feb. 21, 2012.) Thus, it would be beneficial to check disposition of drugs in animals with specific BCRP inhibitors.

SUMMARY

In one aspect, the present disclosure provides compounds that are effective inhibitors of breast cancer resistance protein (BCRP). In some embodiments, BCRP is human BCRP, for example the protein, a homodimer of the protein or a complex comprising the protein described in GenPept Accession number NM_004827, or an isoform thereof, such as GenPept Accession number NM_001257386, or a homodimer thereof or a complex comprising the isoform. These compounds are useful for inhibiting BCRP activity in vitro and in vivo. In one aspect, the compound is (I-1):

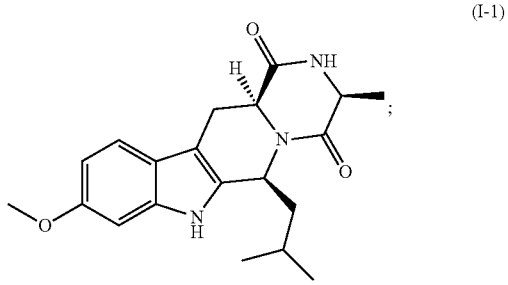

(I-1)

or a pharmaceutically acceptable salt thereof.

In one aspect, the present disclosure relates to pharmaceutical compositions comprising the compound (I-1), or a pharmaceutically acceptable salt thereof, and one or more pharmaceutically acceptable excipients.

In one aspect, the present disclosure relates to methods of inhibiting BCRP or decreasing the activity of BCRP, comprising contacting cells expressing BCRP with a compound which is (I-1) or a pharmaceutically acceptable salt thereof.

In one aspect, the present disclosure relates to methods of determining a potential BCRP substrate comprising providing a sample of cells expressing BCRP and providing a candidate BCRP substrate, contacting the sample of cells with the candidate BCRP substrate in the presence or absence of the compound (I-1) or a pharmaceutically acceptable salt thereof, measuring BCRP-mediated efflux transport in the presence or absence of the compound, and determining the candidate BCRP substrate is a BCRP substrate if efflux is inhibited by the compound (I-1).

In one aspect, the present disclosure provides compounds that are effective inhibitors of BCRP. These compounds are useful for inhibiting BCRP activity in vitro and in vivo. In one aspect, the compound is 8:

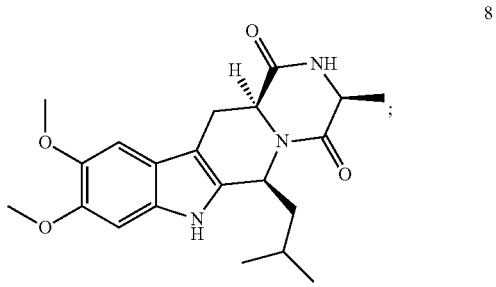

8 or a pharmaceutically acceptable salt thereof.

In one aspect, the present disclosure relates to pharmaceutical compositions comprising the compound 8, or a pharmaceutically acceptable salt thereof, and one or more pharmaceutically acceptable excipients.

In one aspect, the present disclosure relates to methods of inhibiting BCRP or decreasing the activity of BCRP, comprising contacting cells expressing BCRP with a compound which is compound 8 or a pharmaceutically acceptable salt thereof.

In one aspect, the present disclosure relates to methods of determining a potential BCRP substrate comprising providing a sample of cells expressing BCRP and providing a candidate BCRP substrate, contacting the sample of cells with the candidate BCRP substrate in the presence or absence of the compound 8 or a pharmaceutically acceptable salt thereof, measuring BCRP-mediated efflux transport in the presence or absence of the compound, and determining the candidate BCRP substrate is a BCRP substrate if efflux is inhibited by the compound 8.

In one aspect, the present disclosure provides compounds that are effective inhibitors of BCRP. These compounds are useful for inhibiting BCRP activity in vitro and in vivo. In one aspect, the compound is 12:

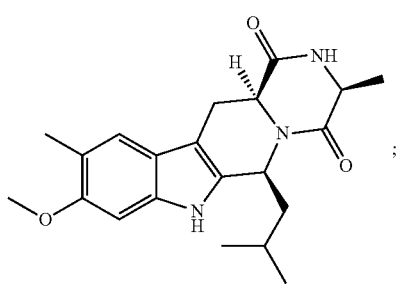

or a pharmaceutically acceptable salt thereof.

In one aspect, the present disclosure relates to pharmaceutical compositions comprising the compound 12, or a pharmaceutically acceptable salt thereof, and one or more pharmaceutically acceptable excipients.

In one aspect, the present disclosure relates to methods of inhibiting BCRP or decreasing the activity of BCRP, comprising contacting cells expressing BCRP with a compound which is compound 12 or a pharmaceutically acceptable salt thereof.

In one aspect, the present disclosure relates to methods of determining a potential BCRP substrate comprising providing a sample of cells expressing BCRP and providing a candidate BCRP substrate, contacting the sample of cells with the candidate BCRP substrate in the presence or absence of the compound 12 or a pharmaceutically acceptable salt thereof, measuring BCRP-mediated efflux transport in the presence or absence of the compound, and determining the candidate BCRP substrate is a BCRP substrate if efflux is inhibited by the compound 12.

DESCRIPTION

Compounds and Definitions

Compounds of the present disclosure include those described generally, such as for example, compound (I-1) above. As used herein, the following definitions shall apply unless otherwise indicated.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the present disclosure. Unless otherwise stated, all tautomeric forms of the compounds of the present disclosure are within the scope of the present disclosure. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of the present disclosure. Such compounds are useful, for example, as analytical tools or probes in biological assays.

The terms "stereoisomer", "enantiomer", "diastereomer", "epimer", and "chiral center", are used herein in accordance with the meaning each is given in ordinary usage by those of ordinary skill in the art. Thus, stereoisomers are compounds that have the same atomic connectivity, but differ in the spatial arrangement of the atoms. Enantiomers are stereoisomers that have a mirror image relationship, that is, the stereochemical configuration at all corresponding chiral centers is opposite. Diastereomers are stereoisomers having more than one chiral center, which differ from one another in that the stereochemical configuration of at least one, but not all, of the corresponding chiral centers is opposite. Epimers are diastereomers that differ in stereochemical configuration at only one chiral center.

It is to be understood that, when a disclosed compound has at least one chiral center, the present disclosure encompasses one enantiomer of the compound, substantially free from the corresponding optical isomer, a racemic mixture of both optical isomers of the compound, and mixtures enriched in one enantiomer relative to its corresponding optical isomer. When a mixture is enriched in one enantiomer relative to its optical isomer, the mixture contains, for example, an enantiomeric excess of at least 50%, 75%, 90%, 95%, 99%, or 99.5%.

The enantiomers of the present disclosure may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support, for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present disclosure encompasses a diastereomer substantially free of other diastereomers, an enantiomeric pair of diastereomers substantially free of other stereoisomers, mixtures of diastereomers, mixtures of enantiomeric pairs of diastereomers, mixtures of diastereomers in which one diastereomer is enriched relative to the other diastereomer(s), and mixtures of enantiomeric pairs of diastereomers in which one enantiomeric pair of diastereomers is enriched relative to the other stereoisomers. When a mixture is enriched in one diastereomer or enantiomeric pair of diastereomers pairs relative to the other stereoisomers, the mixture is enriched with the depicted or referenced diastereomer or enantiomeric pair of diastereomers relative to other stereoisomers for the compound, for example, by a molar excess of at least 50%, 75%, 90%, 95%, 99%, or 99.5%.

As used herein, the term "diastereomeric ratio" refers to the ratio between diastereomers which differ in the stereochemical configuration at one chiral center, relative to a second chiral center in the same molecule. By way of example, a chemical structure with two chiral centers provides four possible stereoisomers: R*R, R*S, S*R, and S*S, wherein the asterisk denotes the corresponding chiral center in each stereoisomer. The diastereomeric ratio for such a mixture of stereoisomers is the ratio of one diastereomer and its enantiomer to the other diastereomer and its enantiomer= (R*R+S*S):(R*S+S*R).

One of ordinary skill in the art will recognize that additional stereoisomers are possible when the molecule has more than two chiral centers. For purposes of the present disclosure, the term "diastereomeric ratio" has identical meaning in reference to compounds with multiple chiral centers as it does in reference to compounds having two chiral centers. Thus, the term "diastereomeric ratio" refers to the ratio of all compounds having R*R or S*S configuration at the specified chiral centers to all compounds having R*S or S*R configuration at the specified chiral centers. For convenience, this ratio is referred to herein as the diastereomeric ratio at the asterisked carbon, relative to the second specified chiral center.

The diastereomeric ratio can be measured by any analytical method suitable for distinguishing between diastereomeric compounds having different relative stereochemical configurations at the specified chiral centers. Such methods include, without limitation, nuclear magnetic resonance (NMR), gas chromatography (GC), and high performance liquid chromatography (HPLC) methods.

The diastereoisomeric pairs may be separated by methods known to those skilled in the art, for example chromatography or crystallization, and the individual enantiomers within each pair may be separated as described above. Specific procedures for chromatographically separating diastereomeric pairs of precursors used in the preparation of compounds disclosed herein are provided the examples herein.

As used herein, the term "BCRP substrate" refers to a drug or other compound whose efflux from a cell is mediated by BCRP. Examples of BCRP substrates include, but are not limited to, estrone-3-sulfate (E3 S), methotrexate, mitoxantrone, imatinib, irinotecan, lapatinib, rosuvastatin, sulfasalazine, topotecan, and any combinations thereof (Notice, *Draft Guidance for Industry on Drug Interaction Studies—Study Design, Data Analysis, Implications for Dosing, and Labeling Recommendations*, 77 FR 9946, Feb. 21, 2012). Further examples of BCRP substrates include daunorubicin, doxorubicin, epirubicin, bisatrene, flavpiridol, etoposide, teniposide 3, 9-aminocamptothecin, gefitinib, diflomotecan, zidovudine, rhodamine 123, SN-38, and any combinations thereof (Ieiri et al., Expert Opin. Drug Metab. Toxicol. 2009, 5(7):703-729; Krishnamurthy, Annu. Rev. Pharmacol. Toxicol. 2006, 46:381-410). Methods of determining whether a given substance is a substrate for BCRP are known in the art. For example, efflux activity of BCRP may be evaluated by monitoring the basolateral-to-apical/apical-to-basolateral (B to A/A to B) efflux ratio of the compounds of interest in a cell or cell line expressing BCRP (Xia, C. Q., et al., Expression, localization and functional characteristics of breast cancer resistance protein in Caco-2 cells. *Drug Met. Disp.*, 33 (5): 637-643 (2005)).

In some embodiments, a compound of the present disclosure is (I-1):

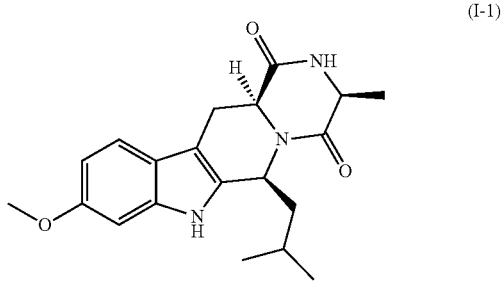

or a pharmaceutically acceptable salt thereof.

In some embodiments, the present disclosure provides a pharmaceutical composition comprising the compound (I-1), or a pharmaceutically acceptable salt thereof and one or more pharmaceutically acceptable excipients.

In some embodiments, a compound of the present disclosure is 8:

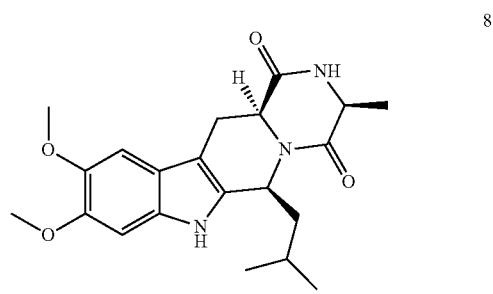

or a pharmaceutically acceptable salt thereof.

In some embodiments, the present disclosure provides a pharmaceutical composition comprising the compound 8, or a pharmaceutically acceptable salt thereof and one or more pharmaceutically acceptable excipients.

In some embodiments, a compound of the present disclosure is 12:

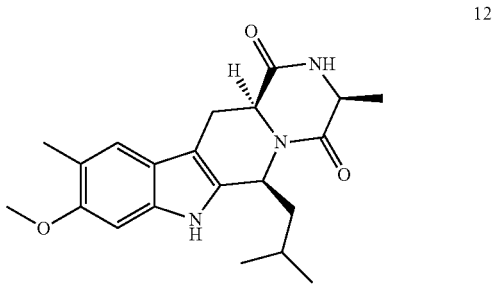

or a pharmaceutically acceptable salt thereof.

In some embodiments, the present disclosure provides a pharmaceutical composition comprising the compound 12, or a pharmaceutically acceptable salt thereof and one or more pharmaceutically acceptable excipients.

In some embodiments, the present disclosure provides a method of decreasing the activity of breast cancer resistance protein (BCRP), comprising contacting cells expressing BCRP or a membrane preparation comprising BCRP, with compound (I-1),

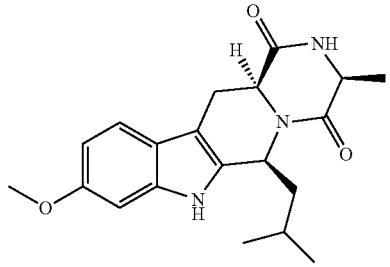

(I-1)

or a pharmaceutically acceptable salt thereof.

In some embodiments, the present disclosure provides a use of the compound (I-1),

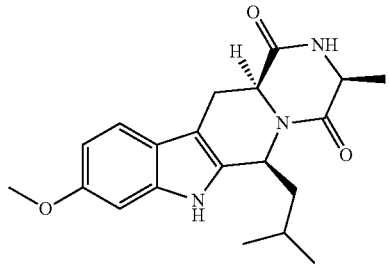

(I-1)

or a pharmaceutically acceptable salt thereof for decreasing the activity of breast cancer resistance protein (BCRP), comprising contacting cells expressing BCRP or a membrane preparation comprising BCRP, with the compound.

In some embodiments, the present disclosure provides a method of decreasing the activity of breast cancer resistance protein (BCRP), comprising contacting a sample of cells expressing BCRP or a membrane preparation comprising BCRP, with compound (I-1),

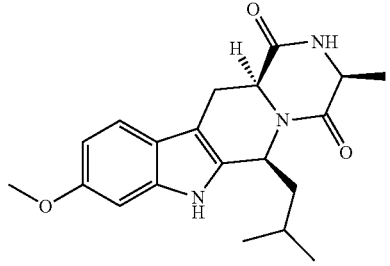

(I-1)

or a pharmaceutically acceptable salt thereof.

In some embodiments, the present disclosure provides a method of inhibiting breast cancer resistance protein (BCRP), comprising contacting cells expressing BCRP or a membrane preparation comprising BCRP with compound (I-1),

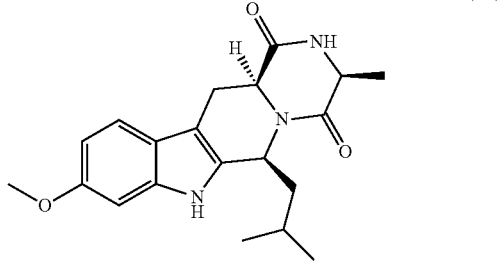

(I-1)

or a pharmaceutically acceptable salt thereof.

In some embodiments, the present disclosure provides a method of inhibiting breast cancer resistance protein (BCRP), comprising contacting a sample of cells expressing BCRP or a membrane preparation comprising BCRP with compound (I-1),

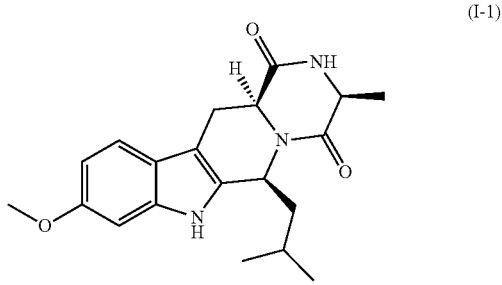

(I-1)

or a pharmaceutically acceptable salt thereof.

In some embodiments, the present disclosure provides a method of inhibiting breast cancer resistance protein (BCRP) in a sample, comprising the steps:

(a) providing a compound which is (I-1):

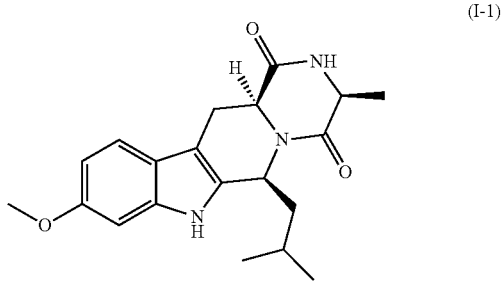

(I-1)

or a pharmaceutically acceptable salt thereof;

(b) providing a sample of cells expressing BCRP; and (c) contacting the sample of (b) with the compound of (a).

In some embodiments, the present disclosure provides a method of determining a potential BCRP substrate, comprising the steps:

(a) contacting a sample of cells expressing BCRP or a membrane preparation comprising BCRP with a candidate BCRP substrate, in the presence or absence of compound (I-1):

(I-1)

[structure of compound (I-1)]

or a pharmaceutically acceptable salt thereof;
(b) measuring BCRP-mediated efflux transport in the presence or absence of the compound; and
(c) determining the candidate BCRP substrate is a BCRP substrate if efflux is inhibited by compound (I-1).

In some embodiments, the present disclosure provides a method of determining a potential BCRP substrate, comprising the steps:
(a) contacting a sample of cells expressing BCRP or a membrane preparation comprising BCRP with a candidate BCRP substrate, in the presence or absence of compound (I-1):

(I-1)

[structure of compound (I-1)]

or a pharmaceutically acceptable salt thereof;
(b) measuring BCRP-mediated efflux transport in the presence or absence of the compound; and
(c) determining the candidate BCRP substrate is a BCRP substrate if efflux measured in the absence of compound (I-1) is more than the efflux measured in the presence of compound (I-1).

In some embodiments, the present disclosure provides a method of determining a potential BCRP substrate, comprising the steps:
(a) providing a sample of cells expressing BCRP;
(b) providing a candidate BCRP substrate;
(c) contacting the sample of (a) with the candidate BCRP substrate of (b), in the presence or absence of compound (I-1):

(I-1)

[structure of compound (I-1)]

or a pharmaceutically acceptable salt thereof;
(d) measuring BCRP-mediated efflux transport in the presence or absence of the compound; and (e) determining the candidate BCRP substrate is a BCRP substrate if efflux is inhibited by compound (I-1).

In some embodiments, the present disclosure provides a method of decreasing the activity of breast cancer resistance protein (BCRP), comprising contacting cells expressing BCRP or a membrane preparation comprising BCRP, with compound 8,

8

[structure of compound 8]

or a pharmaceutically acceptable salt thereof.

In some embodiments, the present disclosure provides a use of compound 8,

8

[structure of compound 8]

or a pharmaceutically acceptable salt thereof for decreasing the activity of breast cancer resistance protein (BCRP), comprising contacting cells expressing BCRP or a membrane preparation comprising BCRP, with the compound.

In some embodiments, the present disclosure provides a method of decreasing activity of breast cancer resistance protein (BCRP), comprising contacting a sample of cells expressing BCRP or a membrane preparation comprising BCRP, with compound 8,

8

[structure of compound 8]

or a pharmaceutically acceptable salt thereof.

In some embodiments, the present disclosure provides a method of inhibiting breast cancer resistance protein (BCRP), comprising contacting cells expressing BCRP or a membrane preparation comprising BCRP with compound 8,

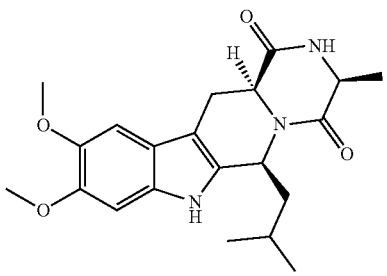

or a pharmaceutically acceptable salt thereof.

In some embodiments, the present disclosure provides a method of inhibiting breast cancer resistance protein (BCRP), comprising contacting a sample of cells expressing BCRP or a membrane preparation comprising BCRP with compound 8,

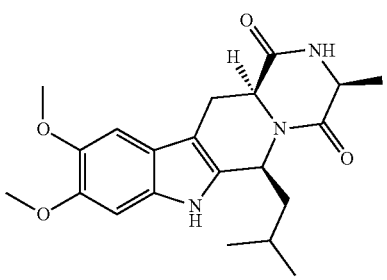

or a pharmaceutically acceptable salt thereof.

In some embodiments, the present disclosure provides a method of inhibiting breast cancer resistance protein (BCRP) in a sample, comprising the steps:
(a) providing a compound which is 8:

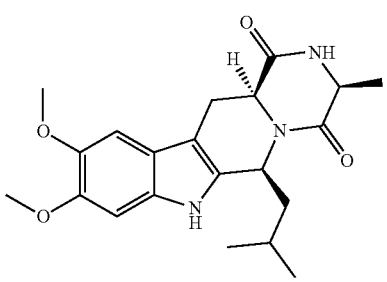

or a pharmaceutically acceptable salt thereof;
(b) providing a sample of cells expressing BCRP; and
(c) contacting the sample of (b) with the compound of (a).

In some embodiments, the present disclosure provides a method of determining a potential BCRP substrate, comprising the steps:

(a) contacting a sample of cells expressing BCRP or a membrane preparation comprising BCRP with a candidate BCRP substrate, in the presence or absence of compound 8:

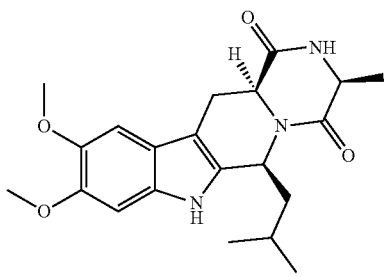

or a pharmaceutically acceptable salt thereof;
(b) measuring BCRP-mediated efflux transport in the presence or absence of the compound; and
(c) determining the candidate BCRP substrate is a BCRP substrate if efflux is inhibited by compound 8.

In some embodiments, the present disclosure provides a method of determining a potential BCRP substrate, comprising the steps:
(a) contacting a sample of cells expressing BCRP or a membrane preparation comprising BCRP with a candidate BCRP substrate, in the presence or absence of compound 8:

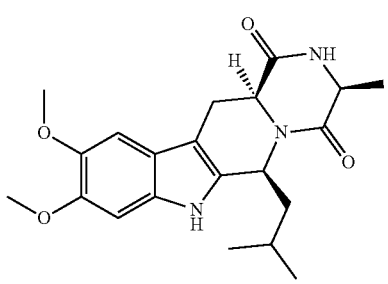

or a pharmaceutically acceptable salt thereof;
(b) measuring BCRP-mediated efflux transport in the presence or absence of the compound; and
(c) determining the candidate BCRP substrate is a BCRP substrate if efflux measured in the absence of compound 8 is more than the efflux measured in the presence of compound 8.

In some embodiments, the present disclosure provides a method of determining a potential BCRP substrate, comprising the steps:
(a) providing a sample of cells expressing BCRP;
(b) providing a candidate BCRP substrate;
(c) contacting the sample of (a) with the candidate BCRP substrate of (b), in the presence or absence of compound 8:

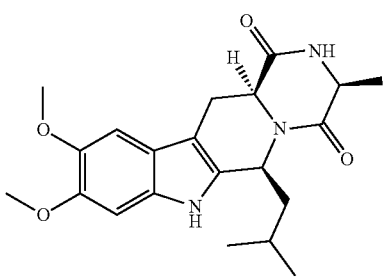

or a pharmaceutically acceptable salt thereof;

(d) measuring BCRP-mediated efflux transport in the presence or absence of the compound; and (e) determining the candidate BCRP substrate is a BCRP substrate if efflux is inhibited by compound 8.

In some embodiments, the present disclosure provides a method of decreasing activity of breast cancer resistance protein (BCRP), comprising contacting cells expressing BCRP or a membrane preparation comprising BCRP, with compound 12,

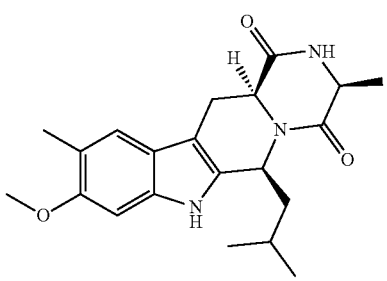

or a pharmaceutically acceptable salt thereof.

In some embodiments, the present disclosure provides a use of compound 12,

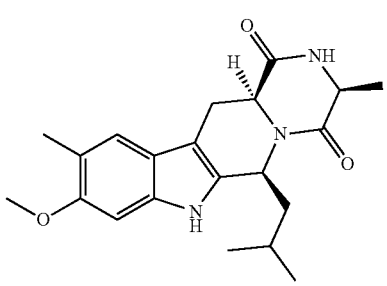

or a pharmaceutically acceptable salt thereof for decreasing activity of breast cancer resistance protein (BCRP), comprising contacting cells expressing BCRP or a membrane preparation comprising BCRP, with the compound.

In some embodiments, the present disclosure provides a method of decreasing the activity of breast cancer resistance protein (BCRP), comprising contacting a sample of cells expressing BCRP or a membrane preparation comprising BCRP, with compound 12,

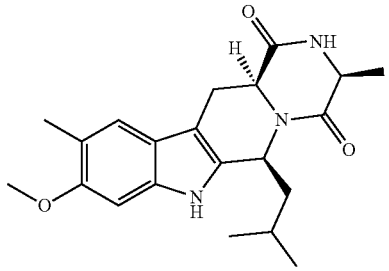

or a pharmaceutically acceptable salt thereof.

In some embodiments, the present disclosure provides a method of inhibiting breast cancer resistance protein (BCRP), comprising contacting cells expressing BCRP or a membrane preparation comprising BCRP with compound 12,

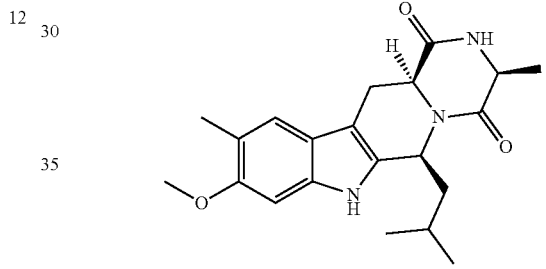

or a pharmaceutically acceptable salt thereof.

In some embodiments, the present disclosure provides a method of inhibiting breast cancer resistance protein (BCRP), comprising contacting a sample of cells expressing BCRP or a membrane preparation comprising BCRP with compound 12,

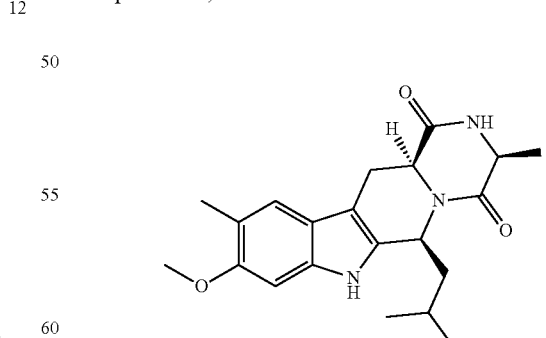

or a pharmaceutically acceptable salt thereof.

In some embodiments, the present disclosure provides a method of inhibiting breast cancer resistance protein (BCRP) in a sample, comprising the steps:

(a) providing a compound which is 12:

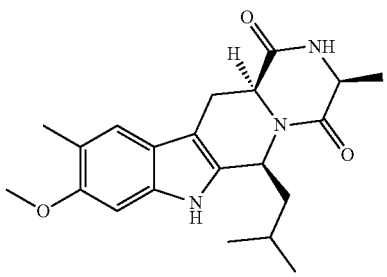

or a pharmaceutically acceptable salt thereof;
(b) providing a sample of cells expressing BCRP; and
(c) contacting the sample of (b) with the compound of (a).

In some embodiments, the present disclosure provides a method of determining a potential BCRP substrate, comprising the steps:
(a) contacting a sample of cells expressing BCRP or a membrane preparation comprising BCRP with a candidate BCRP substrate, in the presence or absence of compound 12:

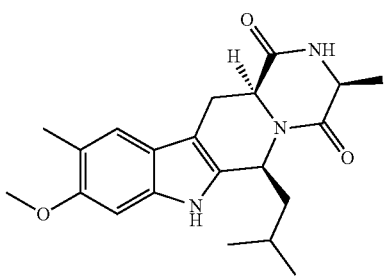

or a pharmaceutically acceptable salt thereof;
(b) measuring BCRP-mediated efflux transport in the presence or absence of the compound; and
(c) determining the candidate BCRP substrate is a BCRP substrate if efflux is inhibited by compound 12.

In some embodiments, the present disclosure provides a method of determining a potential BCRP substrate, comprising the steps:
(a) contacting a sample of cells expressing BCRP or a membrane preparation comprising BCRP with a candidate BCRP substrate, in the presence or absence of compound 12:

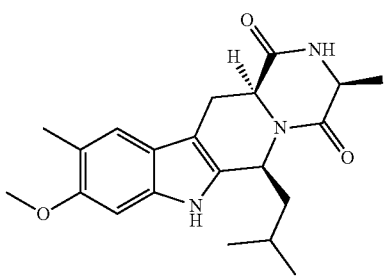

or a pharmaceutically acceptable salt thereof;
(b) measuring BCRP-mediated efflux transport in the presence or absence of the compound; and
(c) determining the candidate BCRP substrate is a BCRP substrate if efflux measured in the absence of compound 12 is more than the efflux measured in the presence of compound 12.

In some embodiments, the present disclosure provides a method of determining a potential BCRP substrate, comprising the steps:
(a) providing a sample of cells expressing BCRP;
(b) providing a candidate BCRP substrate;
(c) contacting the sample of (a) with the candidate BCRP substrate of (b), in the presence or absence of compound 12:

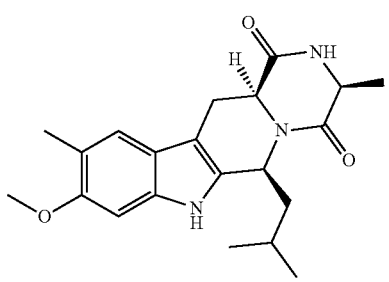

or a pharmaceutically acceptable salt thereof;
(d) measuring BCRP-mediated efflux transport in the presence or absence of the compound; and
(e) determining the candidate BCRP substrate is a BCRP substrate if efflux is inhibited by compound 12.

As used herein, the "net flux ratio" is a number derived from dividing the efflux, e.g. of a transporter in a cell membrane, e.g., an endogenously expressed transporter, from basolateral to apical direction by the efflux from apical to basolateral direction, i.e., the "efflux ratio." Alternatively, the net flux ratio is the efflux ratio of a method using a cell, e.g., exogenously, expressing or over-expressing the transporter divided by the efflux ratio of a method using a control cell not expressing or not over-expressing the transporter. While a transporter can be considered active with a net flux ratio of greater than 1, however, features of the cell system may render this value non-discriminative, e.g., if other transporters are present. If a ratio of greater than 1, between 1 and 2 or 2 is deemed non-discriminative as supported by experience with the cell system used, a net flux ratio of greater than 2 or a ratio calculated relative to positive controls may be used to avoid false positives. A further way to discriminate false positives is if the net flux ratio can be inhibitable by transporter inhibitors. The reduction of the net flux ratio significantly (e.g., by more than 50%) or to 1 by a transporter inhibitor indicates that the transporter is inhibited.

In some embodiments, the method of decreasing the activity of BCRP further comprises providing a BCRP substrate. In some embodiments, the method of decreasing the activity of BCRP further comprises measuring the net flux ratio. In some embodiments the method of decreasing the activity of BCRP decreases the net flux ratio to 1. In some embodiments, the net flux ratio is decreased by more than 50% from the ratio in the absence of inhibitor.

In some embodiments, the method of inhibiting BCRP further comprises providing a BCRP substrate. In some embodiments, the method of inhibiting BCRP further comprises measuring the net flux ratio. In some embodiments, the net flux ratio of a BCRP inhibitor is 1. In some embodiments, the net flux ratio of a BCRP inhibitor is less than 1. In some embodiments, the net flux ratio reduction by a BCRP inhibitor is greater than 50% compared to the net flux ratio in the absence of inhibitor.

In some embodiments, the method of determining a potential BCRP substrate further comprises comparing the efflux of a candidate BCRP substrate with the efflux of a known BCRP substrate, such as E3S. In some embodiments, the method of determining a potential BCRP substrate further comprises measuring the net flux ratio. In some embodiments, the net flux ratio of a BCRP substrate is greater than 1. In other embodiments, the net flux ratio of a BCRP substrate is greater than 2.

In some embodiments, the sample of cells comprises BCRP-expressing cells. In some embodiments, the cells are in vivo. In some embodiments, the cells are in vitro. In some embodiments, the sample of cells comprises human cells. In some embodiments, the sample of cells comprises human cells from a patient. In some embodiments, the sample of cells comprises animal cells. In some embodiments, the sample of cells comprises non-human mammalian cells. In some embodiments, the sample of cells comprises monkey cells. In some embodiments, the sample of cells comprises dog cells. In some embodiments, the sample of cells comprises rat cells. In some embodiments, the sample of cells comprises mouse cells.

In some embodiments, the sample of cells comprises BCRP-overexpressing cells. In some embodiments, the sample of cells comprises BCRP-overexpressing polarized epithelial cell line cells. In some embodiments, the sample of cells comprises intestinal enterocytes, hepatocytes, kidney proximal tubule cells, brain endothelial cells, placental cells, stem cells, mammary gland cells, breast epithelial or blood vessel cells. In some embodiments, the sample of cells comprises Caco-2 cells.

In some embodiments, the sample of cells is a transgenic non-human animal, e.g., a mouse, rat or rabbit, engineered to express or overexpress BCRP in one or more of its cells or tissues. In some embodiments, the sample of cells is a transgenic non-human animal which expresses human BCRP. In some embodiments, BCRP engineered for expression in a transgenic animal replaces the endogenous BCRP normally expressed in that animal or in a particular tissue of the animal. A tissue-specific regulatory sequence(s) can be operably linked to a transgenic BCRP coding sequence in order to direct BCRP expression to particular cells or tissues, such as the gastrointestinal tract. Methods for making such transgenic animals are known in the art.

In some embodiments, the methods of the present disclosure may be used with membrane preparations of cells expressing BCRP. In some embodiments, the membrane preparations are from bacterial cells expressing BCRP. In some embodiments, the membrane preparations are from insect cells expressing BCRP. In some embodiments, the membrane preparations are from Sf9 insect cells expressing BCRP.

In some embodiments, the methods of the present disclosure may be used with BCRP-expressing cells in culture, e.g. in vitro, e.g., in a sample, a biopsy or cells from a patient having a cancer, ex vivo, or in situ. In some embodiments, cells that express BCRP (e.g., cells collected by biopsy of a tumor or metastatic lesion; cells from an established cancer cell line; or recombinant cells), can be cultured in vitro in culture medium and the contacting step can be effected by adding the BCRP inhibitor compound and/or the BCRP substrate to the culture medium. In some embodiments, the methods of the present disclosure may be used with cancer cells. In some embodiments, the methods of the present disclosure may be used with leukemia cells or cells from solid tumors such as cells from adenocarcinomas of the digestive tract, endometrium, lung and melanoma. In some embodiments, the methods of the present disclosure may also be used with BCRP-expressing cells in vivo.

In some embodiments, the method of present disclosure comprises measuring the net flux ratio of the candidate BCRP substrate in the presence and absence of compound (I-1).

In some embodiments, the method of present disclosure comprises measuring the net flux ratio of the candidate BCRP substrate in the presence and absence of compound 8.

In some embodiments, the method of present disclosure comprises measuring the net flux ratio of the candidate BCRP substrate in the presence and absence of compound 12.

In some embodiments, the compound of the present disclosure exhibits high bioavailability and low clearance in vivo.

Synthetic Process

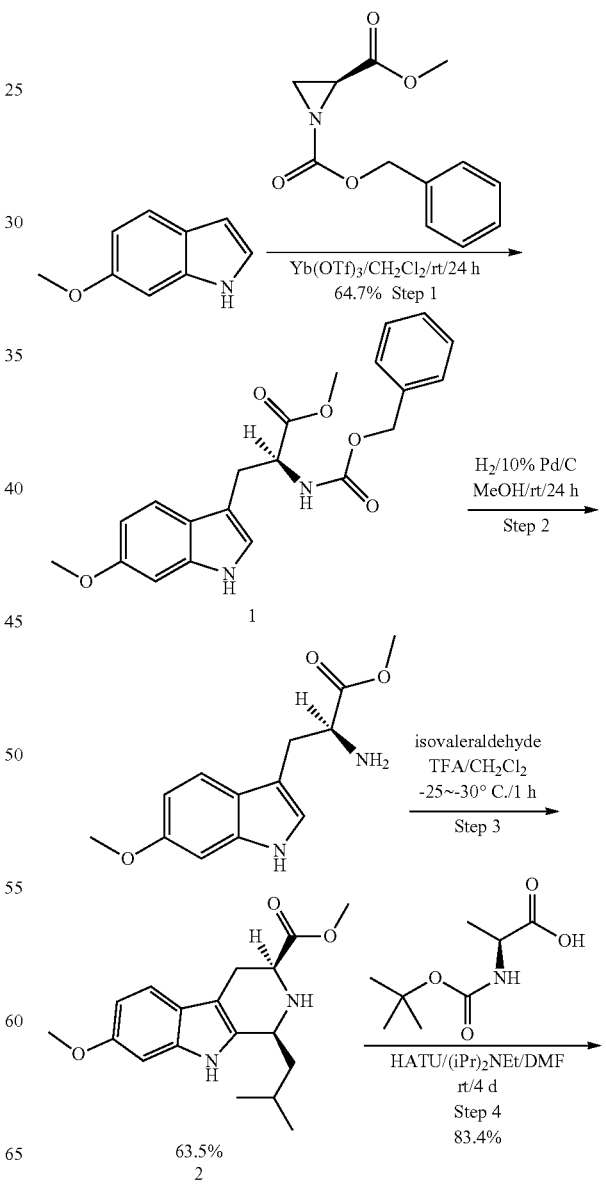

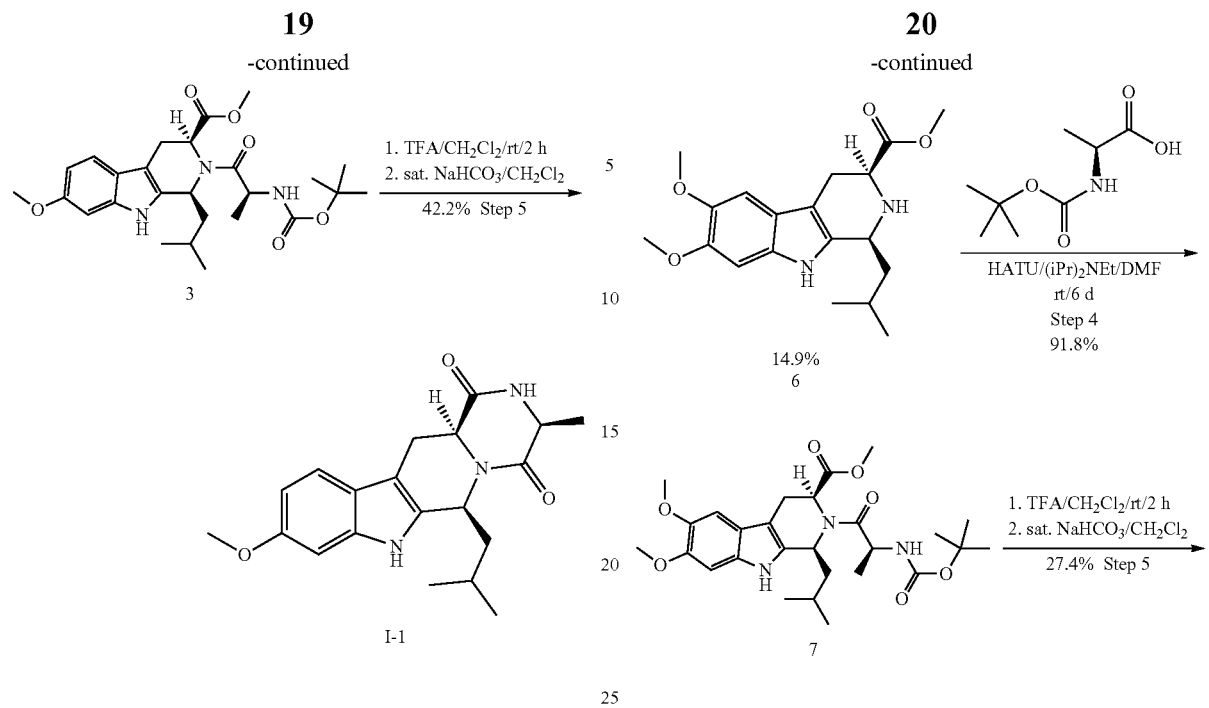
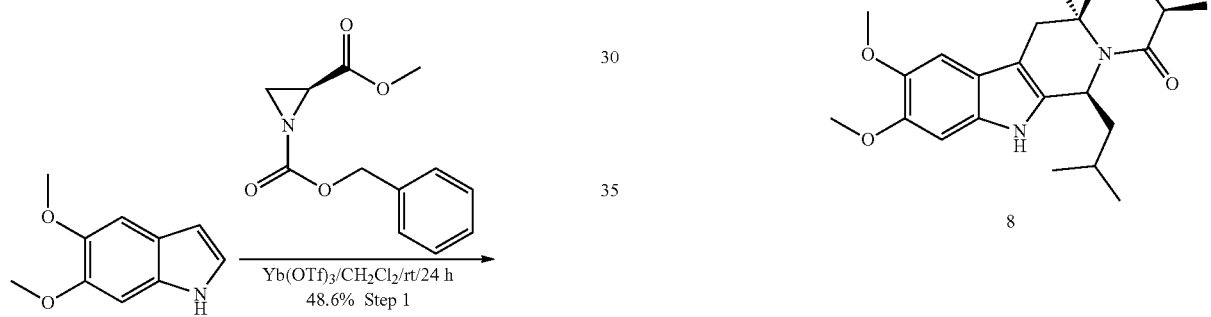
Scheme 2 - Synthesis of 8
Scheme 3 - Synthesis of 12
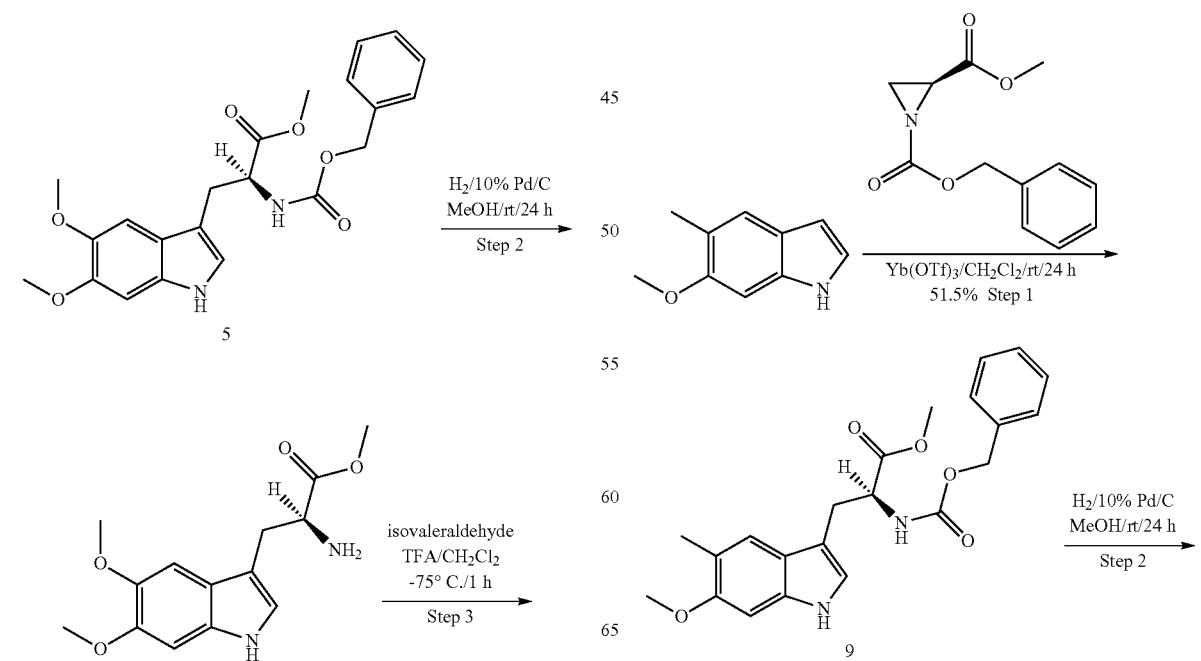

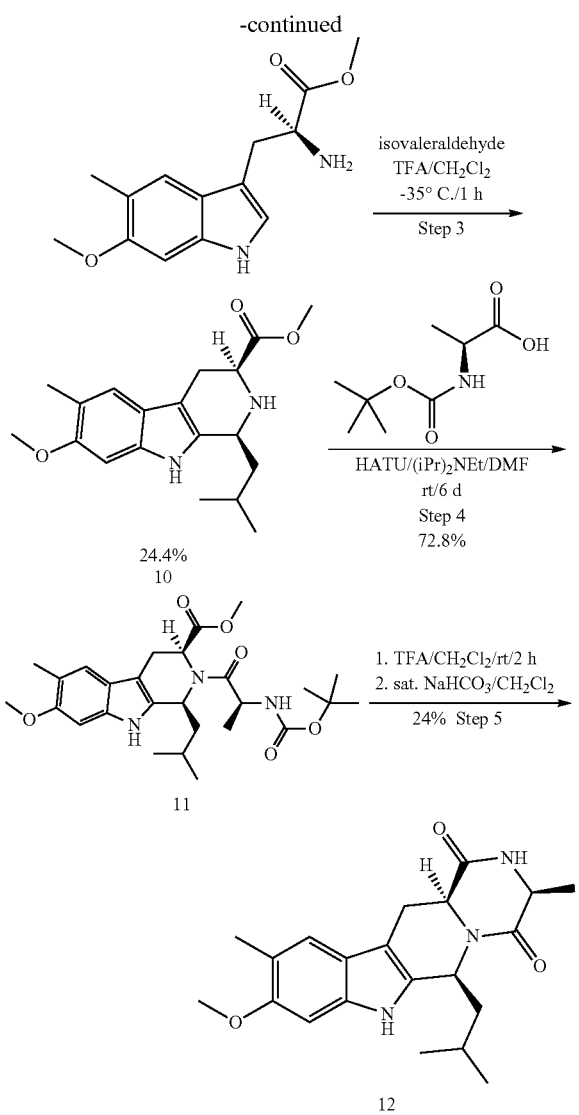

Scheme 1 outlines an exemplary process for the preparation of Compound I-1. Scheme 2 outlines an exemplary process for preparation of Compound 8, and Scheme 3 outlines an exemplary process for preparation of Compound 12. Steps 1-3 of the sequences shown may be performed as described in Li et al. (Tetrahedron Lett., 2008, 49, 1480).

In some embodiments, the present disclosure provides a method for the synthesis of the compound (I-1) from the compound 2 comprising the steps:

(4) a peptide coupling between compound 2 and a Boc-protected amino acid; and (5) removal of the Boc protecting group; followed by cyclization.

In some embodiments, the present disclosure provides a method for the synthesis of the compound 8 from the compound 6 comprising the steps:

(4) a peptide coupling between compound 8 and a Boc-protected amino acid; and (5) removal of the Boc protecting group; followed by cyclization.

In some embodiments, the present disclosure provides a method for the synthesis of the compound 12 from the compound 10 comprising the steps:

(4) a peptide coupling between compound 12 and a Boc-protected amino acid; and (5) removal of the Boc protecting group; followed by cyclization.

As in the sequences shown in Scheme 1, Scheme 2 and Scheme 3, the peptide coupling shown in Step 4 provides a Boc-Alanine precursor for cyclization in the following step.

In some embodiments, the peptide coupling of Step 4 is effected by the coupling reagent HATU (O-(7-azabenzotriazol-1-yl)-N,N,N',N'-tetramethyluronium hexafluorophophate). In some embodiments, the peptide coupling can also be effected, for example, in the presence of a suitable coupling reagent, such as, for example, HBTU (O-(benzotriazol-1-yl)-N,N,N',N'-tetramethyluronium hexafluorophophate), TBTU ((O-(benzotriazol-1-yl)-N,N,N',N'-tetramethyluronium tetrafluoroborate), EDC (1-[3-(dimethylaminopropyl]-3-ethylcarbodiimide), CTP (2-chloro-1,3-dimethylimidazoldinium hexafluorophosphate), BOP (Benzotriazol-1-yloxy)tris(dimethylamino) phosphonium hexafluorophosphate, or BEP (2-bromo-1-ethyl-pyridinium tetrafluoroborate).

In some embodiments, the peptide coupling of Step 4 is effected by the coupling reagent in the organic solvent DMF (N,N-dimethylformamide). This peptide coupling can also be effected in an organic solvent such as, for example, THF (tetrahydrofuran), DMSO (dimethylsulfoxide), DCM (dichloromethane), chloroform, NMP (1-methyl-2-pyrrolidinone), or DMAC (N,N-dimethylacetamide).

In some embodiments, the peptide coupling of Step 4 is effected in the presence of a base such as (iPr)$_2$NEt (DIPEA; N,N-diisopropylethylamine). This step can also be effected in the presence of another tertiary amine base such as, for example, NEt$_3$ (triethylamine), diethylamine, pyridine, DBU (1,8-diazabicyclo[5.4.0]-undec-7-ene), morpholine, or DABCO (1,4-diazabicyclo[2.2.2]octane).

As in Scheme 1, Scheme 2 and Scheme 3, the cyclization in Step 5 results in the preparation of Compound (I-1), Compound 8, and Compound 12, respectively. In one embodiment, the Boc amino acid is removed in the presence of an acid, followed by cyclization in the presence of a weak base.

In some embodiments, removal of the Boc group in Step 5 (1) is effected in the presence of TFA (trifluoroacetic acid). Removal of the protecting group can also be effected, for example, in the presence of an acid, such as HCl (hydrochloric acid), H$_2$SO$_4$ (sulfuric acid), HNO$_3$ (nitric acid), or H$_3$PO$_4$ (phosphoric acid).

In some embodiments, the removal of the Boc group in Step 5 (1) is effected in an organic solvent such as CH$_2$Cl$_2$ (DCM). This removal can also be effected in an organic solvent such as, for example, EtOAc (ethyl acetate), chloroform, ether, dibutyl ether, or MTBE (t-butyl methyl ether).

In some embodiments, cyclization in Step 5 (2) to generate Compound (I-1), Compound 8 or Compound 12 can be effected in the presence of saturated NaHCO$_3$ (sodium bicarbonate). Cyclization can also be effected, for example, in the presence of a weak base, such as NEt$_3$ (triethylamine), diethylamine, pyridine, (iPr)$_2$NEt (N,N-diisopropylethylamine), DBU (1,8-diazabicyclo[5.4.0]-undec-7-ene), morpholine, DABCO (1,4-diazabicyclo[2.2.2]octane, Na$_2$CO$_3$ (sodium carbonate), or NaOH (sodium hydroxide).

If a pharmaceutically acceptable salt of the BCRP inhibitor is utilized in these compositions, the salt preferably is derived from an inorganic or organic acid or base. For reviews of suitable salts, see, e.g., Berge et al, *J. Pharm. Sci.*

66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" or "pharmaceutically acceptable excipient" is used herein to refer to a material that is compatible with a recipient subject, and is suitable for delivering an active agent to the target site without terminating the activity of the agent. In some embodiments, the subject is a mammal, for example, a human. In some embodiments, the toxicity or adverse effects, if any, associated with the carrier are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy*, 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the present disclosure, such as by producing any undesirable biological effect or otherwise interacting in a deleterious manner with any other component(s) of the pharmaceutically acceptable composition, its use is contemplated to be within the scope of the present disclosure. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the present disclosure can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

According to a preferred embodiment, the compositions of the present disclosure are formulated for pharmaceutical administration to a mammal, preferably a human being. Such pharmaceutical compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the present disclosure may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial- and/or viral-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of the present disclosure with suitable nonirritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the present disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the present disclosure can be prepared by methods known to one of ordinary skill in the art and/or by reference to the schemes shown below and the synthetic examples. Exemplary synthetic routes are set forth below in the Examples.

In order that the present disclosure be more fully understood, the following preparative and testing examples are set forth. These examples are not to be construed as limiting the scope of the present disclosure in any way.

EXAMPLES

Abbreviations and Nomenclature

AA ammonium acetate
ACN acetonitrile
d doublet
dd doublet of doublets
DMF N, N-dimethylformamide
DMSO dimethylsulfoxide
EtOAc ethyl acetate
FA formic acid
J coupling constant
hr hours
Hz hertz
(iPr)$_2$NEt Diisopropylethylamine
LAH lithium aluminum hydride
LCMS liquid chromatography mass spectrum
LDA lithium diisopropylamide
m multiplet
MeOH methanol
s singlet
t triplet
THF tetrahydrofuran
q quartet Example 1

Synthetic Methods and Analytical Data

Overall synthetic schemes are represented in Scheme 1 (Compound I-1), Scheme 2 (Compound 8), and Scheme 3 (Compound 12).

All reagents were obtained from Sigma-Aldrich, with the exception of 6-methoxyindole (Combi-Blocks, IN-0054). Deuterated NMR solvents were obtained from Cambridge Isotope Laboratories, Inc. All reactions were monitored using Agilent 1100 Series LC/MS.

LCMS data are obtained using an Agilent 1100 LC (column: Luna, 5 µm C18(2) 150×4.6 mm) and an Agilent mass spectrometer.

NMR spectrum is shown by proton NMR, using a 300 MHz Bruker Avance spectrometer equipped with a 5 mm QNP probe and a 400 MHz Bruker Avance II spectrometer equipped with a 5 mm QNP probe for the measurement; δ values are expressed in ppm.

Preparation of (S)-methyl 2-(benzyloxycarbonylamino)-3-(6-methoxy-1H-indol-3-yl)propanoate (1)

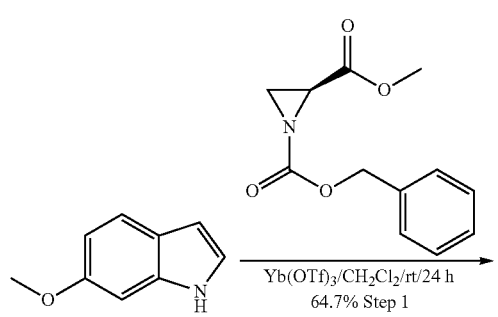

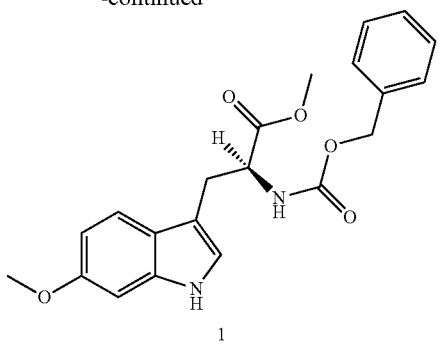

In a 1 L two-neck round bottom flask, after drying under N$_2$ gas for 1 hour, 6-methoxyindole (18.750 g, 127.40 mmol) was dissolved in methylene chloride (240 mL) at room temperature. To the reaction mixture, 1-benzyl 2-methyl (S)-(−)-1,2-aziridinedicarboxylate (15 g, 63.77 mmol) and ytterbium(III) triflate (39.38 g, 63.48 mmol) were added in 3 portions every 90 min. The reaction flask was wrapped with aluminum foil (product is light-sensitive) and stirred at room temperature for 24 hours. After checking for completion by HPLC, the reaction mixture was washed with water (240 mL, 3×) and the combined organic layer was dried over MgSO$_4$, concentrated by rotary-evaporation, and purified by flash column chromatography on silica gel using a hexanes/ethyl acetate gradient. The fractions containing the product were combined and concentrated in vacuo to yield (1) as yellow oil (15.77 g, 64.7%).

Preparation of (S)-methyl 2-(benzyloxycarbonylamino)-3-(5,6-dimethoxy-1H-indol-3-yl)propanoate (5)

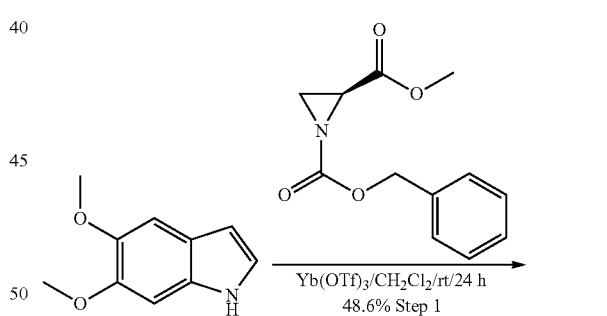

Compound 5 was prepared in a similar manner to that described for compound 1 (48.6% yield).

Preparation of (S)-methyl 2-(benzyloxycarbonylamino)-3-(6-dimethoxy-5-methyl-1H-indol-3-yl)propanoate (9)

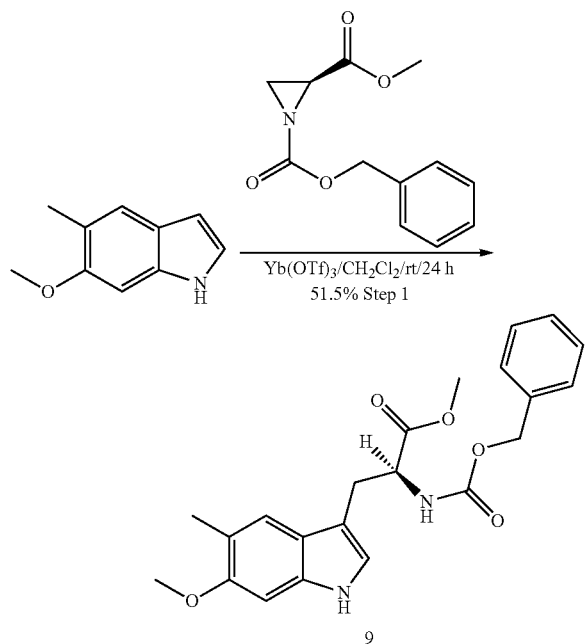

Compound 9 was prepared in a similar manner to that described for compound 1 (51.5% yield).

Preparation of (1S,3S)-methyl-1-isobutyl-7-methoxy-2,3,4,9-tetrahydro-1H-beta-carboline-3-carboxylate (2) and (1S,3R)-methyl-1-isobutyl-7-methoxy-2,3,4,9-tetrahydro-1H-beta-carboline-3-carboxylate (2A)

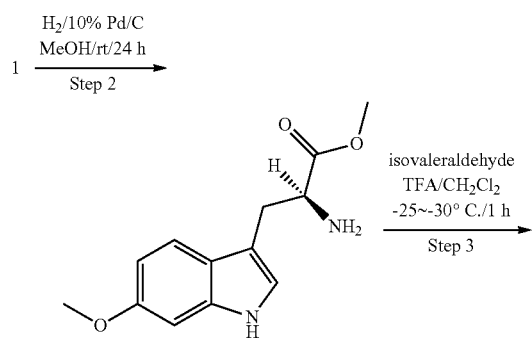

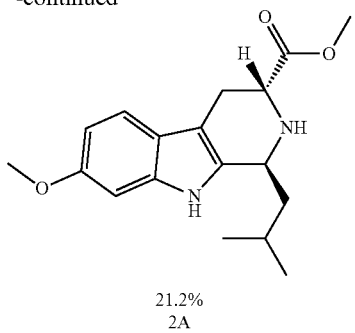

In a 1 L round bottom flask, (S)-methyl 2-{[(benzyloxy)carbonyl]amino}-3-(6-methoxy-1H-indol-3-yl)propanoate (12.94 g, 33.838 mmol), 10% Pd/C (217 mg, 2.04 mmol) were added in methanol (346.8 mL). The flask was attached to a high vacuum and was evacuated and filled with hydrogen from a hydrogen balloon attached to the high vacuum. The reaction mixture was allowed to stir at room temperature. After 24 hours, the reaction mixture was checked for completion by HPLC, filtered through celite to remove the catalyst, diluted with water (90 mL), and washed with methylene chloride (90 mL, 3×). The combined organic layer was dried over MgSO$_4$ and concentrated under vacuum to yield the deprotected amine intermediate as light brown oil.

The resulting residue, (S)-methyl 2-amino-3-(6-methoxy-1H-indol-3-yl)propanoate, was dissolved in methylene chloride (135.53 mL) under nitrogen and cooled to −25~−30° C. with dry ice and ethanol bath. Isovaleraldehyde (4.72 mL, 44.0 mmol) was added and stirred for 5 minutes. Trifluoroacetic acid (3.39 mL, 44.0 mmol) was added and the reaction was monitored by TLC and HPLC. After 1 hour, the reaction mixture was quenched with sat. NaHCO$_3$ (136 mL), extracted with methylene chloride (136 mL, 3×), dried over MgSO$_4$. The product was purified by flash column chromatography using a hexanes/ethyl acetate gradient to give 2 as a metallic light yellow powder (6.798 g, 63.5% yield) and 2A as a light yellow powder (2.266 g, 21.2% yield).

Preparation of (1S,3S)-methyl-1-isobutyl-6,7-dimethoxy-2,3,4,9-tetrahydro-1H-beta-carboline-3-carboxylate (6) and (1S,3R)-methyl-1-isobutyl-6,7-dimethoxy-2,3,4,9-tetrahydro-1H-beta-carboline-3-carboxylate (6A)

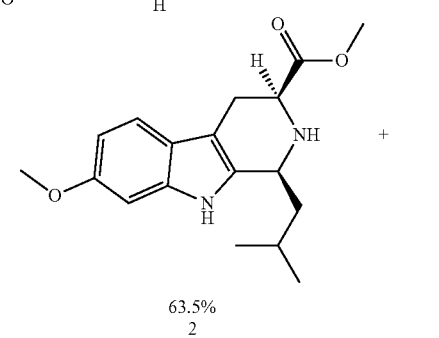

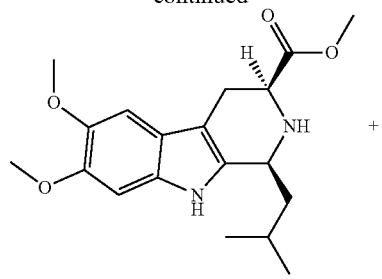

14.9%
6

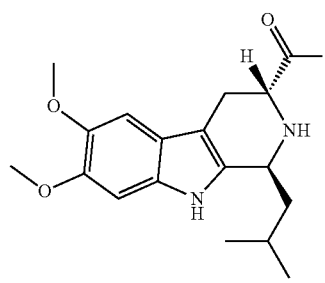

40%
6A

Compound 6 and compound 6A were prepared in a similar manner to that described for compound 2 and compound 2A (14.9% yield for compound 6 and 40% yield for compound 6A).

Preparation of (1S,3S)-methyl-1-isobutyl-7-methoxy-6-methyl-2,3,4,9-tetrahydro-1H-beta-carboline-3-carboxylate (10) and (1S,3R)-methyl-1-isobutyl-7-methoxy-6methyl-2,3,4,9-tetrahydro-1H-beta-carboline-3-carboxylate (10A)

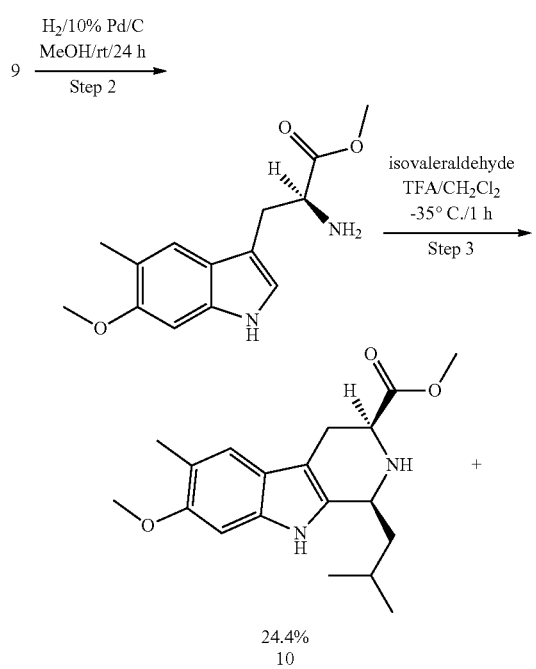

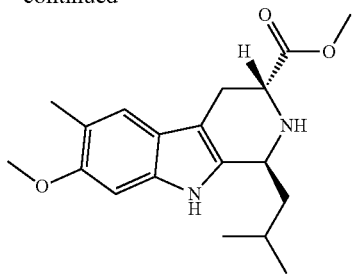

39.6%
10A

Compound 10 and compound 10A were prepared in a similar manner to that described for compound 2 and compound 2A (24.4% yield for compound 10 and 39.6% yield for compound 10A).

Preparation of (1S,3S)-methyl 2-((2S)-2-(tert-butoxycarbonylamino)propanoyl)-1-isobutyl-7-methoxy-2,3,4,9-tetrahydro-1H-beta-carboline-3-carboxylate (3)

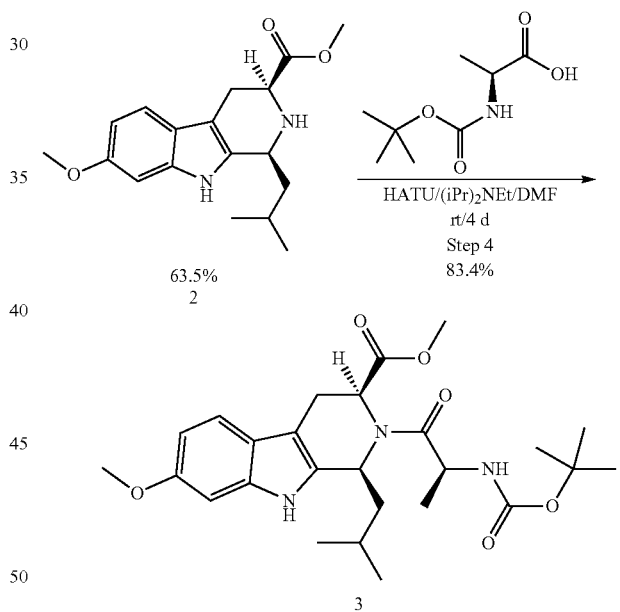

A 50 mL round bottom flask containing a solution of (1S,3S)-methyl-1-isobutyl-7-methoxy-2,3,4,9-tetrahydro-1H-beta-carboline-3-carboxylate (750.000 mg, 2.37046 mmol), N-(tert-butoxycarbonyl)-L-alanine (673 mg, 3.56 mmol), HATU (1400 mg, 3.6 mmol) in N,N-dimethylformamide (12 mL, 160 mmol) was cooled to 0° C. N,N-Diisopropylethylamine (0.619 mL, 3.56 mmol) was added. The reaction mixture was stirred at room temperature for 24 hours. Second and third portions of N-(tert-butoxycarbonyl)-L-alanine, HATU, N,N-diisopropylethylamine were each added after 24 hours and the reaction mixture was stirred for an additional 24 hours. After four days, the reaction was checked for completion by HPLC. The reaction mixture was diluted with water (12 mL) and extracted with methylene chloride (12 mL, 3x). The combined organic layer was dried over MgSO$_4$, concentrated in vacuo at 40~50° C. with an oil bath to remove N,N-diisopropylethylamine and N,N-dimethylformamide. The resulting residue was purified by flash column chromatography using a hexanes/ethyl acetate gradient to yield (3) as light brown oil (1.061 g, 83.4%).

$^1$H NMR (300 MHz, CDCl$_3$) δ 7.57 (s, 1H), 7.31 (d, J=8.6 Hz, 1H), 6.82-6.67 (m, 1H), 5.55 (m, 1H), 4.84 (m, 1H), 4.14-3.98 (q, 1H), 3.76 (s, 3H), 3.64 (s, 3H), 3.49 (d, J=15.6 Hz, 2H), 3.16 (m, 1H), 2.97 (m, 1H), 1.98 (d, J=1.3 Hz, 6H), 1.39 (s, 9H), 1.30 (dd, J=8.2, 5.8 Hz, 3H), 1.19 (m, 3H).

$^{13}$C NMR (75 MHz, CDCl$_3$) δ 171.38, 171.12, 156.67, 155.04, 137.08, 131.97, 120.83, 118.92, 109.54, 104.83, 95.20, 60.57, 55.85, 53.11, 48.99, 47.40, 45.02, 28.44, 25.31, 22.37, 19.69, 14.33.

Preparation of (1S,3S)-methyl 2-((2S)-2-(tert-butoxycarbonylamino)propanoyl)-1-isobutyl-6,7-dimethoxy-2,3,4,9-tetrahydro-1H-beta-carboline-3-carboxylate (7)

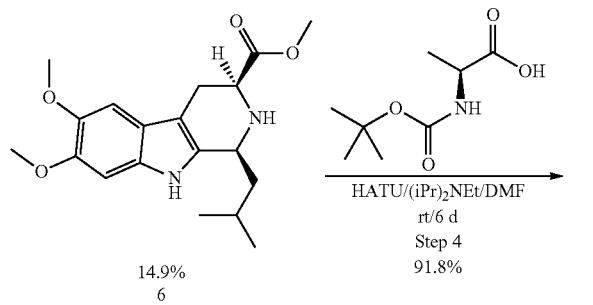

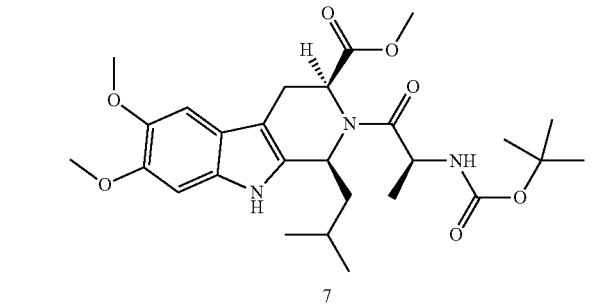

Compound 7 was prepared in a similar manner to that described for compound 3 (91.8% yield).

$^1$H NMR (300 MHz, CDCl$_3$) δ 10.47 (s, 1H), 7.07 (d, J=7.7 Hz, 1H), 6.96 (d, J=12.7 Hz, 1H), 6.84 (d, J=11.3 Hz, 1H), 5.61 (s, 1H), 5.27 (d, J=6.5 Hz, 1H), 4.63 (s, 1H), 3.74 (d, J=2.5 Hz, 6H), 3.61-3.54 (m, 3H), 3.33-3.27 (m, 2H), 1.85-1.73 (m, 2H), 1.70-1.46 (m, 1H), 1.45-1.39 (m, 3H), 1.37-1.30 (m, 9H), 1.02 (dd, J=12.4, 6.0 Hz, 3H), 0.89 (dd, J=13.9, 6.2 Hz, 3H).

$^{13}$C NMR (75 MHz, CDCl$_3$) δ 172.10, 170.76, 155.14, 146.59, 144.60, 132.39, 130.89, 119.37, 104.04, 101.46, 95.88, 78.44, 60.19, 56.54, 56.27, 52.68, 52.37, 47.93, 45.20, 28.65, 28.57, 28.40, 24.44, 23.87, 21.20, 17.50, 14.53.

Preparation of (1S,3S)-methyl 2-((2S)-2-(tert-butoxycarbonylamino)propanoyl)-1-isobutyl-7-methoxy-6-methyl-2,3,4,9-tetrahydro-1H-beta-carboline-3-carboxylate (11)

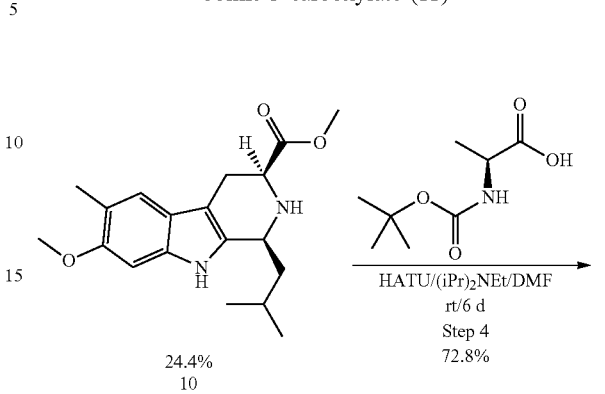

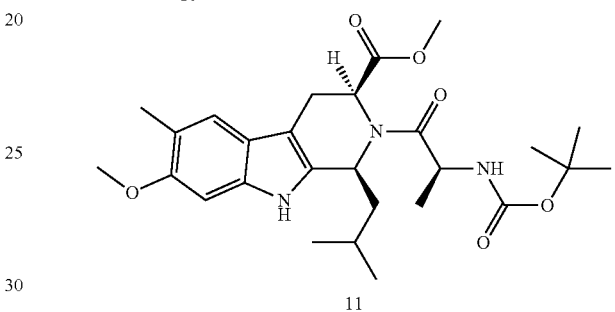

Compound 11 was prepared in a similar manner to that described for compound 3 (72.8% yield).

$^1$H NMR (300 MHz, CDCl$_3$) δ 10.48 (s, 1H), 7.14 (s, 1H), 6.84-6.78 (m, 1H), 6.77 (s, 1H), 5.60 (s, 1H), 5.25 (d, J=6.6 Hz, 1H), 4.62 (d, J=8.0 Hz, 1H), 3.90 (t, J=7.5 Hz, 6H), 3.56 (s, 2H), 2.18 (d, J=0.9 Hz, 3H), 1.46-1.42 (m, 2H), 1.41 (d, J=2.1 Hz, 1H), 1.37 (s, 9H), 1.25 (dddq, J=2.9, 1.7, 1.2, 0.6 Hz, 3H), 1.02-0.85 (m, 6H).

$^{13}$C NMR (75 MHz, CDCl$_3$) δ 175.07, 170.74, 155.67, 154.23, 135.83, 132.09, 120.12, 119.13, 117.90, 103.61, 93.44, 78.33, 60.17, 55.64, 52.64, 49.23, 47.91, 45.15, 28.64, 28.57, 28.37, 24.44, 21.21, 21.17, 21.15, 17.48, 14.50.

Preparation of (3S,6S,12aS)-6-isobutyl-9-methoxy-3-methyl-2,3,6,7,12,12a-hexahydropyrazino[1',2':1,6]pyrido[3,4-b]indole-1,4-dione (Compound (I-1))

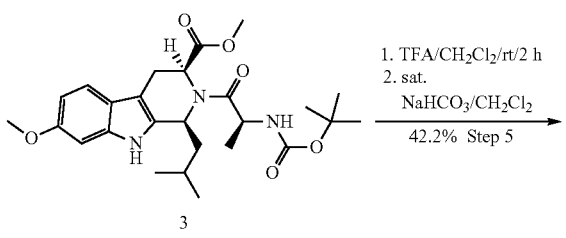

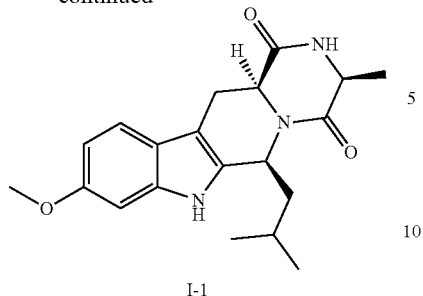

I-1

In a 250 mL round bottom flask, (1S,3S)-methyl 2-((2S)-2-(tert-butoxycarbonylamino)propanoyl)-1-isobutyl-7-methoxy-2,3,4,9-tetrahydro-1H-beta-carboline-3-carboxylate (690 mg, 1.4 mmol) was dissolved in DCM (11 mL, 170 mmol) and trifluoroacetic acid (11 mL, 140 mmol) was added dropwise at 0° C. The reaction mixture was stirred at 0° C. for 15 minutes and room temperature for 1=2 hours while being monitored by HPLC. When complete, all volatiles were removed by rotary-evaporation for 30 min to give a dark purple residue. The resulting residue was dissolved in 20 mL methylene chloride and washed with sat. NaHCO$_3$ (20 mL, 2×) until the pH of the aqueous layer was 10. The combined organic layer was dried over MgSO$_4$, concentrated under vacuum, and purified by flash column chromatography using a hexanes/ethyl acetate gradient to yield Compound (I-1) as light yellow powder (211 mg, 42.2% yield).

$^1$H NMR (300 MHz, CDCl$_3$) δ 7.82 (s, 1H), 7.44 (d, J=8.7 Hz, 1H), 6.89 (d, J=2.1 Hz, 1H), 6.83 (dd, J=8.6, 2.2 Hz, 1H), 5.89 (s, 1H), 5.44 (dd, J=9.3, 4.3 Hz, 1H), 4.13-4.02 (m, 2H), 3.85 (s, 3H), 3.52 (dd, J=15.8, 4.8 Hz, 1H), 3.04 (dd, J=15.9, 11.8 Hz, 1H), 1.84-1.71 (m, 1H), 1.56 (d, J=6.8 Hz, 3H), 1.25 (dd, J=8.0, 6.3 Hz, 2H), 1.07 (d, J=6.4 Hz, 3H), 0.83 (d, J=6.3 Hz, 3H).

$^{13}$C NMR (75 MHz, CDCl$_3$) δ 170.45, 169.56, 156.52, 136.67, 133.31, 120.75, 118.81, 109.71, 106.52, 95.36, 56.13, 55.89, 51.21, 50.31, 45.98, 24.96, 23.96, 21.89, 21.86, 16.61.

HRMS m/z: calcd 356.1969 (M+1). found 356.1985 (M+1).

Preparation of (3S,6S,12aS)-6-isobutyl-9,10-dimethoxy-3-methyl-2,3,6,7,12,12a-hexahydropyrazino[1',2':1,6]pyrido[3,4-b]indole-1,4-dione (8)

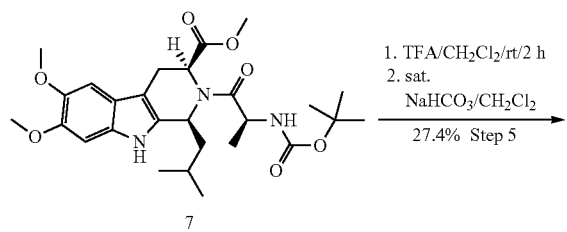

7

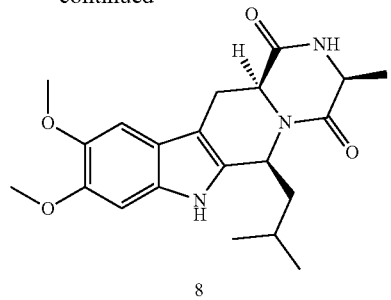

8

Compound 8 was prepared in a similar manner to that described for compound I-1 (27.4% yield).

$^1$H NMR (300 MHz, CDCl$_3$) δ 10.73 (s, 1H), 8.31 (s, 1H), 7.08 (s, 1H), 6.87 (s, 1H), 5.28 (dd, J=8.4, 4.4 Hz, 1H), 4.14-4.07 (m, 1H), 4.07-3.98 (m, 1H), 3.74 (d, J=1.3 Hz, 6H), 2.76 (dd, J=15.7, 11.7 Hz, 1H), 2.48 (q, J=1.9 Hz, 2H), 1.56 (td, J=8.8, 4.3 Hz, 1H), 1.51-1.37 (m, 2H), 1.28 (d, J=6.8 Hz, 3H), 0.91 (d, J=6.3 Hz, 3H), 0.73 (d, J=6.3 Hz, 3H).

$^{13}$C NMR (75 MHz, CDCl$_3$) δ 170.17, 170.17, 146.47, 144.85, 133.61, 130.38, 119.22, 105.63, 101.32, 95.93, 56.43, 56.19, 55.75, 50.45, 49.58, 46.35, 24.60, 24.20, 22.51, 21.95, 16.19.

HRMS m/z: calcd 386.2074 (M+1). found 386.2080 (M+1).

Preparation of (3S,6S,12aS)-6-isobutyl-9-methoxy-3,10-dimethyl-2,3,6,7,12,12a-hexahydropyrazino[1',2':1,6]pyrido[3,4-b]indole-1,4-dione (12)

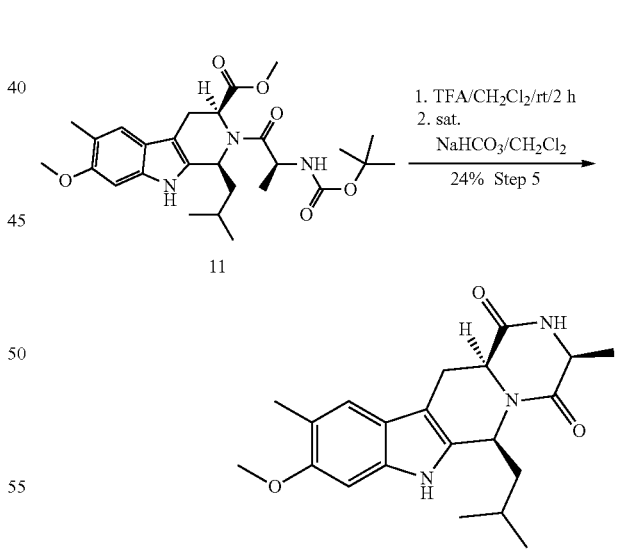

11

12

Compound 12 was prepared in a similar manner to that described for compound I-1 (24% yield).

$^1$H NMR (300 MHz, CDCl$_3$) δ 10.75 (s, 1H), 8.33 (s, 1H), 7.23 (d, J=1.0 Hz, 1H), 6.82 (s, 1H), 5.28 (dd, J=8.2, 4.5 Hz, 1H), 4.15-4.07 (m, 1H), 4.06-3.97 (m, 1H), 3.77 (s, 3H), 3.25 (dd, J=15.7, 5.2 Hz, 1H), 2.82-2.69 (m, 1H), 2.19 (d, J=0.9 Hz, 3H), 1.52 (ddd, J=17.7, 8.5, 4.5 Hz, 2H), 1.42

(ddd, J=6.9, 4.8, 3.2 Hz, 1H), 1.28 (d, J=6.8 Hz, 3H), 0.90 (d, J=6.3 Hz, 3H), 0.73 (d, J=6.3 Hz, 3H).

$^{13}$C NMR (75 MHz, CDCl$_3$) δ 170.22, 170.18, 154.12, 135.38, 133.39, 119.95, 119.12, 118.31, 105.11, 93.60, 55.66, 55.62, 50.41, 49.57, 46.27, 24.58, 24.21, 22.56, 21.79, 17.21, 16.18.

HRMS m/z: calcd 370.2125 (M+1). found 370.2129 (M+1).

Preparation of (3S,6S,12aR)-6-isobutyl-9-methoxy-3-methyl-2,3,6,7,12,12a-hexahydropyrazino[1',2':1,6]pyrido[3,4-b]indole-1,4-dione (4)

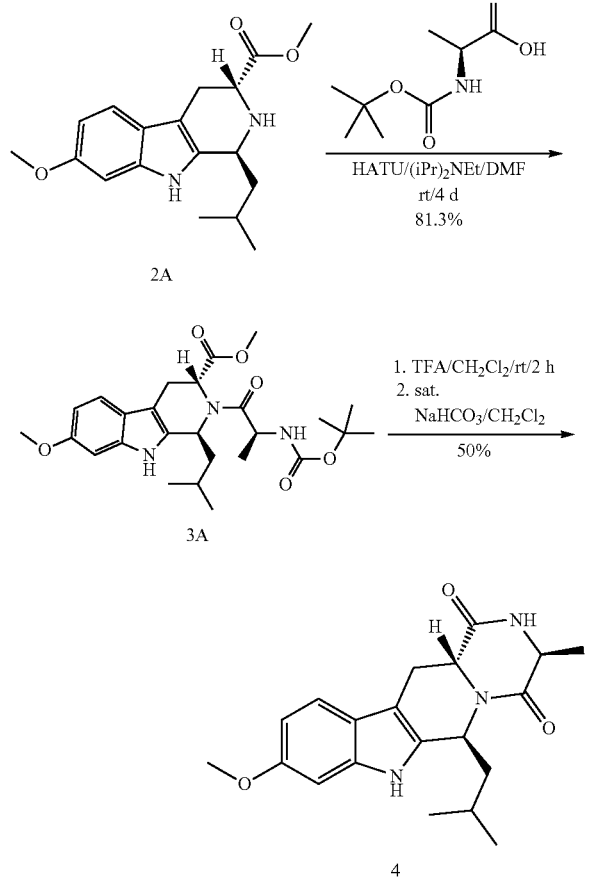

Compound 3A was prepared in a similar manner to that described for compound 3 (81.3% yield). Compound 4 was prepared in a similar manner to that described above for Compound (I-1).

Yield=50%.

$^1$H NMR (300 MHz, CDCl$_3$) δ 7.74 (s, 1H), 7.33 (d, J=8.5 Hz, 1H), 6.85 (d, J=2.0 Hz, 1H), 6.79 (dd, J=8.6, 2.2 Hz, 1H), 6.42 (s, 1H), 5.92-5.82 (m, 1H), 4.40 (dd, J=11.9, 4.2 Hz, 1H), 4.28-4.17 (m, 1H), 3.84 (s, 3H), 3.42 (dd, J=15.4, 4.3 Hz, 1H), 2.96-2.83 (m, 1H), 1.88-1.68 (m, 2H), 1.63 (dd, J=8.4, 4.7 Hz, 2H), 1.54 (d, J=7.0 Hz, 3H), 1.10 (d, J=6.3 Hz, 3H), 0.99 (d, J=6.4 Hz, 3H).

$^{13}$C NMR (75 MHz, CDCl$_3$) δ 167.80, 165.85, 156.83, 136.89, 132.23, 120.85, 118.83, 109.62, 106.40, 95.17, 55.88, 52.81, 51.77, 48.04, 43.68, 28.21, 25.35, 23.43, 23.17, 22.56.

HRMS m/z: calcd 356.1969 (M+1). found 356.1986 (M+1).

Preparation of (3S,6S,12aR)-6-isobutyl-9,10-dimethoxy-3-methyl-2,3,6,7,12,12a-hexahydropyrazino[1',2':1,6]pyrido[3,4-b]indole-1,4-dione (8A)

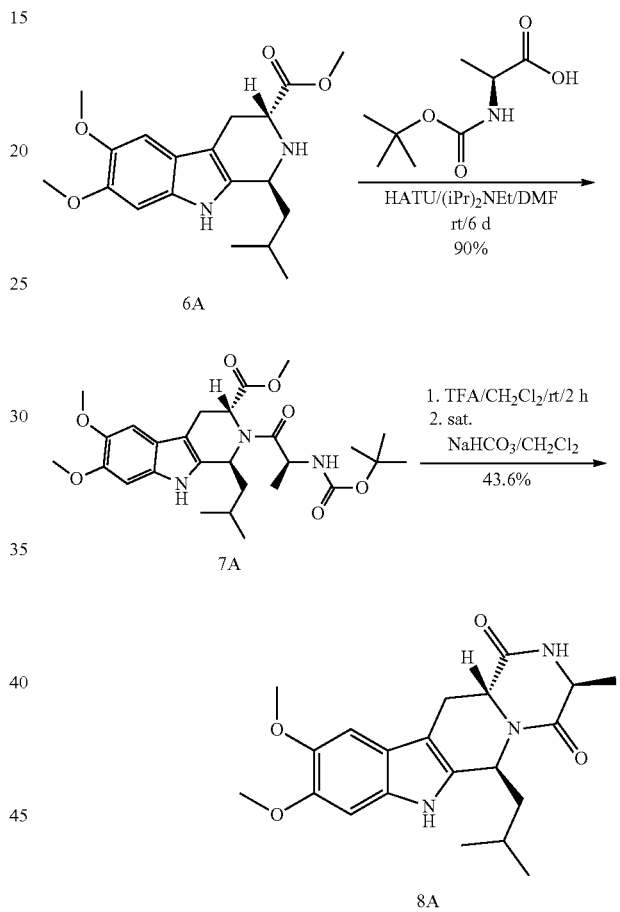

Compound 7A was prepared in a similar manner to that described for compound 7 (90% yield). Compound 8A was prepared in a similar manner to that described above for Compound 8.

Yield=43.6%.

$^1$H NMR (300 MHz, CDCl$_3$) δ 10.66 (s, 1H), 8.41 (s, 1H), 6.95 (s, 1H), 6.84 (s, 1H), 5.67 (d, J=9.6 Hz, 1H), 4.28-4.15 (m, 1H), 4.02 (d, J=4.6 Hz, 1H), 3.73 (d, J=5.1 Hz, 7H), 3.17 (dd, J=9.4, 4.7 Hz, 1H), 2.78-2.64 (m, 1H), 1.79 (t, J=10.3 Hz, 1H), 1.59 (s, 2H), 1.31 (d, J=6.9 Hz, 3H), 1.02 (d, J=5.3 Hz, 3H), 0.89 (d, J=5.5 Hz, 3H).

$^{13}$C NMR (75 MHz, CDCl$_3$) δ 166.88, 166.56, 146.68, 144.71, 132.96, 130.58, 119.33, 105.18, 101.44, 95.82, 56.47, 56.26, 52.44, 50.87, 47.59, 42.93, 28.23, 25.07, 23.84, 22.76, 22.49.

HRMS m/z: calcd 386.2074 (M+1). found 386.2074 (M+1).

Preparation of (3S,6S,12aR)-6-isobutyl-9-methoxy-3,10-dimethyl-2,3,6,7,12,12a-hexahydropyrazino[1',2':1,6]pyrido[3,4-b]indole-1,4-dione (12A)

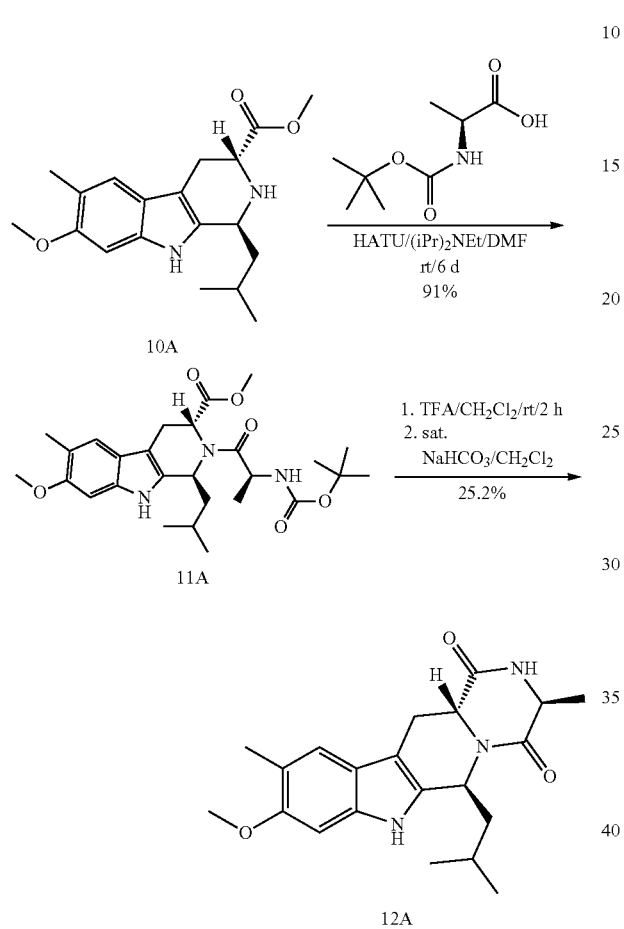

Compound 11A was prepared in a similar manner to that described for compound 11 (91% yield). Compound 12A was prepared in a similar manner to that described above for Compound 12.

Yield=25.2%.

$^1$H NMR (300 MHz, CDCl$_3$) δ 10.69 (s, 1H), 8.45-8.38 (m, 1H), 7.12 (d, J=1.0 Hz, 1H), 6.79 (s, 1H), 5.71-5.64 (m, 1H), 4.23 (dd, J=11.8, 4.3 Hz, 1H), 4.06-3.97 (m, 1H), 3.76 (s, 3H), 3.12 (dd, J=15.3, 4.3 Hz, 1H), 2.75-2.68 (m, 1H), 2.17 (d, J=0.8 Hz, 3H), 1.80 (t, J=10.3 Hz, 1H), 1.57 (tt, J=9.2, 4.4 Hz, 2H), 1.31 (d, J=7.0 Hz, 3H), 1.02 (d, J=5.7 Hz, 3H), 0.89 (d, J=6.0 Hz, 3H).

$^{13}$C NMR (75 MHz, CDCl$_3$) δ 166.86, 166.57, 154.33, 135.56, 132.75, 120.08, 119.17, 118.16, 104.70, 93.45, 55.67, 52.40, 50.86, 47.54, 42.84, 28.08, 25.08, 23.84, 22.76, 22.49, 17.17.

HRMS m/z: calcd 370.2125 (M+1). found 370.2129 (M+1).

Example 2

Characteristics of Compound (I-1), Compound 8, and Compound 12

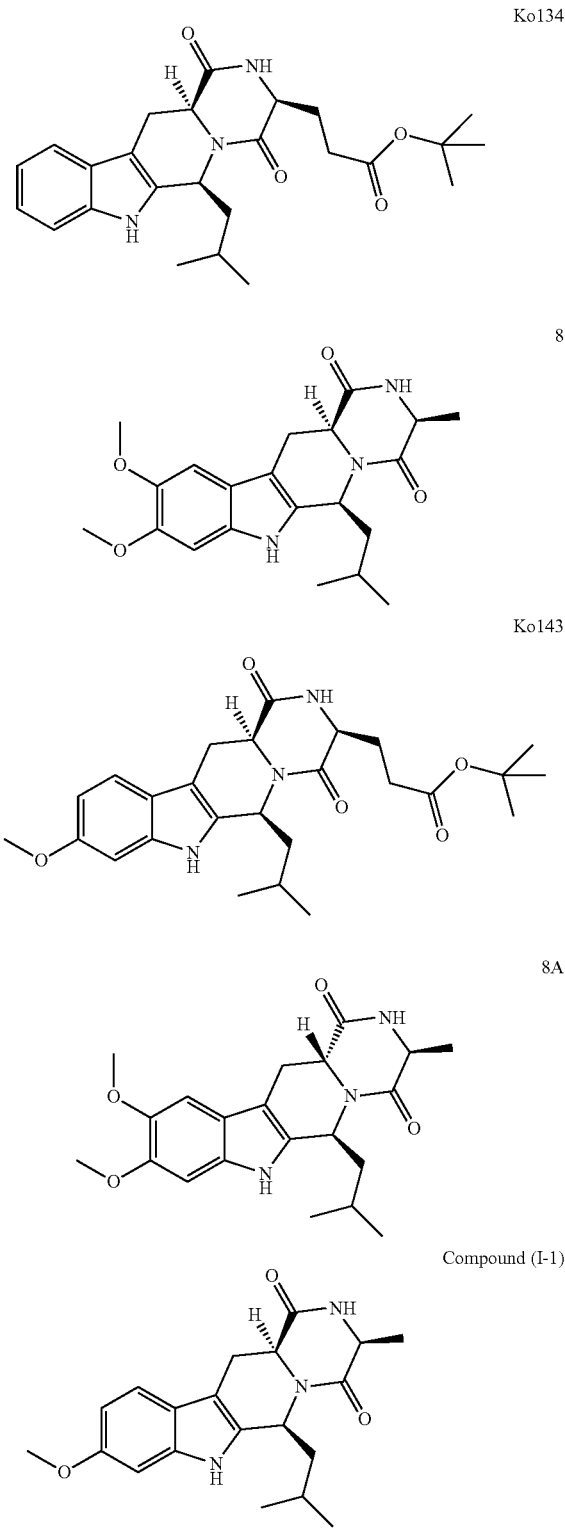

12

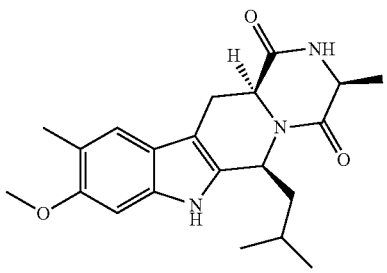

4

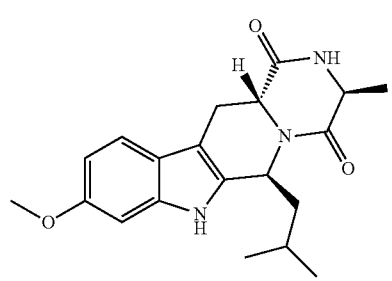

12A

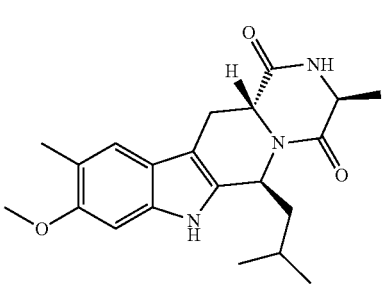

Determination of $IC_{50}$ on BCRP and P-Gp Transporters

Compounds Ko134 and Ko143 referenced in the Tables can be prepared according to the methods in Li et al. (*Tetrahedron Lett.*, 2008, 49, 1480). Compounds (I-1), 4, 8, 8A, 12 and 12A are prepared as shown above.

To determine potency of compounds on inhibition of transporters, bi-directional transport studies are performed in Caco-2 cells (American Type Culture Collection, Manassas, Va.) at 37° C. in air, according to Xia et al. (Expression, localization and functional characteristics of breast cancer resistance protein in Caco-2 cells. *Drug Met. Disp.*, 33 (5): 637-643 (2005)). Prior to each experiment, the confluent cell monolayers on Transwell™ inserts are washed and equilibrated for 30 minutes with transport media (Hank's balanced salt solution (HBSS) containing 10 mM of N-2-hydroxyethyl-piperazine-N'-2-ethanesulfonic acid (HEPES) and 10 mM of glucose, pH 7.4). The experiment is initiated by adding a solution containing the $^3$H-digoxin (25 nM, substrate for p-gp), or $^3$H-E3S (17 nM, substrate for BCRP) to either the apical (for A-to-B transport) or basolateral (for B-to-A transport) compartment in the absence or presence of various concentrations of Compound (I-1) or Ko143. At preset time points, 0.05 mL aliquot of receiving solutions are sampled from the basolateral side (for A-to-B transport) or from the apical side (for B-to-A transport), and replaced immediately with an equal amount of fresh transport media except at the last time point (the end of the incubation). The radioactivity in each sample is measured by 1450 MicroBeta TriLux, a microplate scintillation and luminescence counter (PerkinElmer Life Sciences). Radioactivity ($^3$H) of the dosing solution is measured and used to calculate the initial donor concentration of the substrate.

The $IC_{50}$ of Compound (I-1) and of other compounds on BCRP efflux transporter was determined according to this method, and the results are shown in Table 1 and Table 1A.

TABLE 1

| | $IC_{50}$ on BCRP efflux transporter | |
|---|---|---|
| Compound | $IC_{50}$ | $IC_{50}$ of Ko143 |
| Ko134 | 3.25 μM | 0.23 μM |
| Compound (I-1) | 0.60 μM | 0.61 μM |
| 4 | >10 μM | 0.61 μM |

Test system: Caco-2-cells, substrate: 3H-Estrone-3-sulfate (26 nM).

TABLE 1A

| | $IC_{50}$ on BCRP efflux transporter | |
|---|---|---|
| Compound | $IC_{50}$ | $IC_{50}$ of Ko143 |
| 8 | >10 μM | 1.7 μM |
| 8A | >10 μM | 1.7 μM |
| 12 | 1.98 μM | 1.81 μM |
| 12A | >10 μM | 1.81 μM |

Test system: Caco-2-cells, substrate: 3H-Estrone-3-sulfate (26 nM).

The $IC_{50}$ of Compound (I-1) and of Ko143 on P-gp transporter were also determined using this method, and the results shown in Table 2 indicate that Compound (I-1) is a selective BCRP inhibitor.

TABLE 2

| | $IC_{50}$ on P-gp transporter | |
|---|---|---|
| Compound | Ko143 | Compound (I-1) |
| $IC_{50}$ | >30 μM | >30 μM |

Test system: Caco-2-cells.

Determination of CYP Enzyme Inhibition Profile

Human liver microsomes (HLMs) (0.3 mg/mL in 0.1-M potassium phosphate buffer, pH 7.4) are incubated with CYP (cytochromes P450) isozyme-selective substrates (phenacetin for CYP1A2, amodiaquine for CYP2C8, diclofenac for CYP2C9, S-mephenytoin for CYP2C19, Dextromethorphan for CYP2D6, and midalozam for CYP3A4/5), and multiple concentrations of Compound (I-1) or Ko143 (0, 0.041, 0.12, 0.37, 1.11, 3.33, 10, and 30 μM) in 96-well plates. Reactions are initiated by the addition of β-NADPH (2 mM) and $MgCl_2$ (3 mM) in 0.1-M potassium phosphate buffer, pH 7.4. Reactions are incubated for 12 minutes at 37° C., and then terminated by the addition of an equal volume of ACN containing 1-μM carbutamide (IS). The plates are refrigerated at approximately 4° C. for 15 minutes and then centrifuged in order to pellet the precipitated proteins. The supernatants are analyzed by LC/MS/MS for the amount of metabolite formed by each CYP isozyme.

Compound (I-1) and Ko143 were tested according to this method, and their CYP (cytochromes P450) inhibition profiles are as shown in Table 3.

TABLE 3

CYP inhibition

| Compound | IC$_{50}$ (μM) | | | | | |
|---|---|---|---|---|---|---|
| | 1A2 | 2C8 | 2C9 | 2C19 | 2D6 | 3A-M |
| Ko143 | 17.53 | >30 | 6.00 | 14.71 | >30 | >30 |
| Compound (I-1) | 15.38 | >30 | >30 | 18.47 | >30 | >30 |

Determination of In Vivo Pharmacokinetic Profile

To determine pharmacokinetic profile of Compound (I-1) in vivo, Sprague-Dawley rats (Charles River Labs, Worcester, Mass.) are administered 2.0 mg/kg or 20 mg/kg Compound (I-1) or 2.0 mg/kg or 50 mg/kg Ko143, formulated in 0.5% HPMC/0.2% Tween80, via IV or PO respectively. After administration of Compound (I-1) or Ko143, blood is obtained from all animals at predose and at 0.083, 0.25, 0.5, 1, 4, 8, and 24 hours postdose. Approximately 200 μL of whole blood is collected from the jugular vein catheter of each animal into tubes containing the anticoagulant dipotassium ethylenediaminetetraacetic acid (K$_2$EDTA) and is further processed into plasma at approximately 4° C. The concentration of Compound (I-1) or Ko143 in plasma is determined using LC/MS/MS. Pharmacokinetic analysis of the individual plasma concentration data is performed using a nonvalidated program (Phoenix™ WinNonlin®, Version 6.1 [Pharsight Corp (Mountain View, Calif., USA)]).

Compound (I-1) and Ko143 were tested according to this method. Results of this study are shown in Table 4. Compound (I-1) exhibited high bioavailability and low clearance in rats as shown.

While the foregoing disclosure has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the present invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which the present disclosure belongs. The issued patents, applications, GenPept sequences and references that are cited herein are hereby incorporated by reference to the same extent as if each was specifically and individually indicated to be incorporated by reference. In the case of inconsistencies, the present disclosure, including definitions, will control.

What is claimed is:

1. A compound which is:

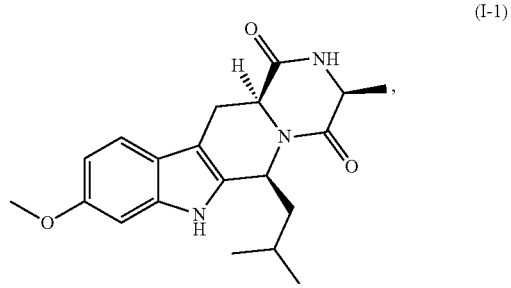

(I-1)

or a pharmaceutically acceptable salt thereof, or

TABLE 4

| Route | Dose (mg/kg) | T$_{1/2}$ (hr) | T$_{max}$ (hr) | C$_{max}$ (nmol/L) | | CL (L/hr/kg) | Vss (L/kg) | F % |
|---|---|---|---|---|---|---|---|---|
| | | | | PK profiles of Ko143 in rats | | | | |
| | | | | | AUC$_{0-24\,hr}$ (hr * nmol/L) | | | |
| IV-JVC | 2 | 0.2 | | | 85.6 | 65.9 | 14.8 | |
| PO-JVC | 50 | | 2 | 21.4 | 72.2 | | | 3 |
| | | | | PK profiles of Compound (I-1) in rats | | | | |
| | | | | | AUC$_{all}$ (hr * nmol/L) | | | |
| IV-JVC | 2 | 0.9 | | | 4000 | 1.54 | 1.64 | |
| PO-JVC | 20 | 2.0 | 1.3 | 10100 | 49000 | | | 123 |

T$_{1/2}$ = half life,
T$_{max}$ = time of maximum drug concentration,
C$_{max}$ = maximum drug concentration,
AUC = area under the concentration,
CL = clearance,
Vss = volume of distribution,
F % = bioavailability,
IV = Intravenous,
JVC = jugular vein cannulation,
PO = per os (by mouth).

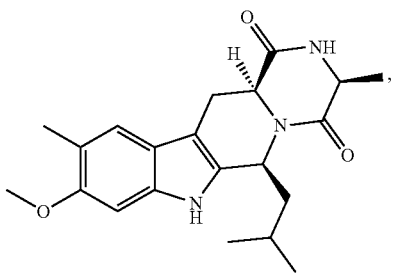

(12)

or a pharmaceutically acceptable salt thereof.

2. The compound of claim 1, wherein the compound is (I-1) or a pharmaceutically acceptable salt thereof.

3. A pharmaceutical composition comprising the compound of claim 1 or a pharmaceutically acceptable salt thereof, and one or more pharmaceutically acceptable excipients.

4. A method of decreasing activity of breast cancer resistance protein (BCRP), comprising contacting cells expressing BCRP or a membrane preparation comprising BCRP, with a compound selected from the group consisting of which is:

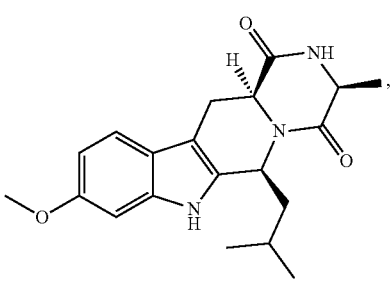

(I-1)

or a pharmaceutically acceptable salt thereof, or

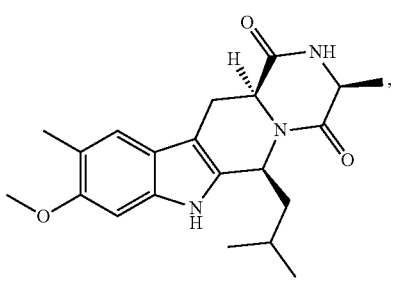

(12)

or a pharmaceutically acceptable salt thereof.

5. The method of claim 4, wherein the cells are in vivo.
6. The method of claim 4, wherein the cells are in vitro.
7. The method of claim 4, wherein the cells comprise at least one cell type chosen from intestinal enterocytes, hepatocytes, kidney proximal tubule cells, brain endothelial cells, placental cells, stem cells, mammary gland cells, breast epithelial, and blood vessel cells.
8. The method of claim 4, wherein the cells comprise cancer cells.
9. The method of claim 4, wherein the cells are Caco-2 cells.
10. The method of claim 4, wherein the cells comprise BCRP-overexpressing cells.
11. The method of claim 4, wherein the cells comprise BCRP-overexpressing polarized epithelial cell line cells.
12. A method of determining a potential BCRP substrate, comprising the steps:
(a) contacting a sample of cells expressing BCRP or a membrane preparation comprising BCRP, with a candidate BCRP substrate, in both the presence and absence of a compound which is:

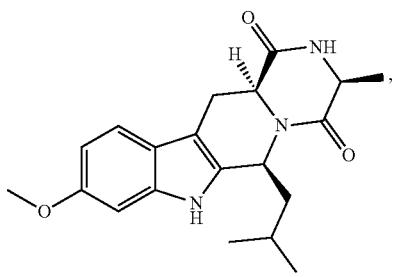

(I-1)

or a pharmaceutically acceptable salt thereof, or

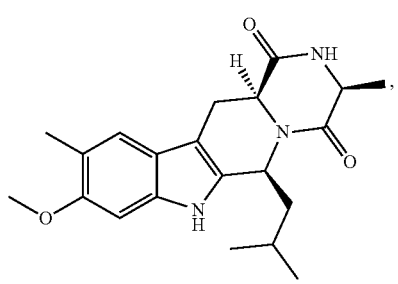

(12)

or a pharmaceutically acceptable salt thereof;
(b) measuring BCRP-mediated efflux transport in both the presence and absence of the compound; and
(c) determining the candidate BCRP substrate is a BCRP substrate if efflux is inhibited by the presence of the compound.
13. The method of claim 12, wherein the sample of cells is in vitro.
14. The method of claim 12, wherein the sample of cells is in vivo.
15. The method of claim 12, wherein the sample of cells comprises at least one cell type chosen from intestinal enterocytes, hepatocytes, kidney proximal tubule cells, brain endothelial cells, placental cells, stem cells, mammary gland cells, breast epithelial and blood vessel cells.
16. The method of claim 12, wherein the sample of cells comprises cancer cells.
17. The method of claim 12, wherein the sample of cells are Caco-2 cells.
18. The method of claim 12, wherein the sample of cells comprises BCRP-overexpressing cells.
19. The method of claim 12, wherein the sample of cells comprises BCRP-overexpressing polarized epithelial cell line cells.
20. The method of claim 12, further comprising measuring the net flux ratio of the candidate BCRP substrate in the presence and absence of the compound.

* * * * *